US011867702B2

(12) United States Patent
Kurzawa-Akanbi et al.

(10) Patent No.: US 11,867,702 B2
(45) Date of Patent: Jan. 9, 2024

(54) DETECTION OF PATHOLOGICAL PROTEIN AGGREGATION

(71) Applicant: UNIVERSITY OF NEWCASTLE UPON TYNE, Newcastle upon Tyne (GB)

(72) Inventors: Marzena Kurzawa-Akanbi, Newcastle upon Tyne (GB); Christopher Mile Morris, Newcastle upon Tyne (GB)

(73) Assignee: UNIVERSITY OF NEWCASTLE UPON TYNE, Newcastle upon Tyne (GB)

( * ) Notice: Subject to any disclaimer, the term of this patent is extended or adjusted under 35 U.S.C. 154(b) by 44 days.

(21) Appl. No.: 16/978,244

(22) PCT Filed: Mar. 5, 2019

(86) PCT No.: PCT/GB2019/050599
§ 371 (c)(1),
(2) Date: Sep. 4, 2020

(87) PCT Pub. No.: WO2019/171035
PCT Pub. Date: Sep. 12, 2019

(65) Prior Publication Data
US 2020/0408782 A1 Dec. 31, 2020

(30) Foreign Application Priority Data
Mar. 6, 2018 (GB) .................................. 1803553.5

(51) Int. Cl.
*G01N 33/68* (2006.01)
(52) U.S. Cl.
CPC . *G01N 33/6896* (2013.01); *G01N 2800/2835* (2013.01)
(58) Field of Classification Search
CPC .................. G01N 33/6896; G01N 2800/2835
See application file for complete search history.

(56) References Cited

FOREIGN PATENT DOCUMENTS

| | | |
|---|---|---|
| JP | 2013504766 A | 2/2013 |
| JP | 2013049662 A | 3/2013 |
| JP | 2016535283 A | 11/2016 |
| JP | 2017067706 A | 4/2017 |
| JP | 2017525976 A | 9/2017 |
| WO | 2013066818 A1 | 5/2013 |
| WO | 2015179875 A1 | 11/2015 |
| WO | 2015200851 A1 | 12/2015 |
| WO | 2016040905 A1 | 3/2016 |
| WO | 2016040907 A1 | 3/2016 |
| WO | 2016164474 A1 | 10/2016 |
| WO | 2017032871 A1 | 3/2017 |
| WO | 2017033152 A1 | 3/2017 |
| WO | 2018007817 A1 | 1/2018 |

OTHER PUBLICATIONS

Cervenakova, et al., Are prions transported by plasma exosomes?, Transfusionand and Apheresis Science (2016) 55:70-83.
Combined Search and Examination Report Great Britain Application No. GB1803553.5 dated Nov. 6, 2018.
Fairfoul, et al., "Alpha-synuclein RT-QuIC in the CSF of patients with alpha-synucleinopaties", Annals of Clinical Translational Neurology, (2016) pp. 1-7.
Ho, et al., "Increased DJ-1 in Urine Exosome of Korean Males with Parkinson's Disease", BioMed Research Internationsl (2014) vol. Article ID 704678, pp. 1-8.
International Search Report Application No. PCT/GB2019/050599 dated May 31, 2019.
Lobb et al., "Optimized exosome isolation protocol for cell culture supernatant and human plasma", Journal of Extracellular Vesicles (2015) 4: 27031 pp. 1-11.
Lööv et al., "a-Synuclein in Extracellular Vesicles: Funtional Implications and Diagnostic Opportunities". Cell Mol. Neuroiol. (2016) 36: pp. 448-448.
Saa et al., "Prion diagnostics by single particle detection and quantitiations", Prion, (2013) vol. 7 Suppl., pp. 19-20.
Saa et al. "Protein misfolding cyclic amplification (PMCA): Current status and future directions", Virus Research (2015) 207: pp. 47-61.
Sano et al., "Prion-Like Seeding of Misfolded a-Synuclein in the Brains of Demential with Lewy Body Patients in RT-QUIC", Mol. Neurobiol. (2018) 55: pp. 3916-3930.
Shi et al., "Plasma exosomal a-synuclein is likely CNS-derived and increased in Parkinson's disease", Acta Neuropathol (2014) 128: pp. 639-659.
Stuendl et al., "Induction of a-synuclein aggregate formation by CSF exosomes from patients with Parkinson's disease and dementia with Lewy bodies", Brain (2016) 139: pp. 481-494.
Great Britain Examination Report Application No. GB1803553.5 dated Nov. 6, 2018.
Wardel et al., "Clinical and genetic characteristics of non-Asian dentatorubrual-pallidoluysian atrophy: A systematic review", Official Journal of the International Parkinson and Movement Disorder Society (2009).
Pagan et al., "The diagnosis and natural history of Huntinton disease", Handbook of Clinical Neurology (2017) vol. 114, pp. 63-67.
Isas et al., "Formation and Structure of Wild Type Huntingtin Exon-1 Fibrils" (2017) 56:28, pp. 3579-3586.
Ruggeri et al., "Infrared nanospectroscopy characterization of oligomeric and fibrillar aggregates during amyloid formation" Nature Communications (2015) 6:7831, pp. 1-9.

(Continued)

Primary Examiner — Olga N Chernyshev
(74) Attorney, Agent, or Firm — Troutman Pepper Hamilton Sanders LLP (Rochester)

(57) ABSTRACT

The present invention provides novel methods of identifying, monitoring or determining the risk of developing a protein misfolding neurodegenerative disorder in a subject, particularly an alpha synucleinopathy (including Parkinson's disease and dementia with Lewy bodies) using extracellular vesicle samples. Corresponding methods for selecting a treatment and assaying for the presence of a pathological prion-like protein (or one or more ceramide species) in an extracellular vesicle sample are also provided.

9 Claims, 25 Drawing Sheets

(56) References Cited

OTHER PUBLICATIONS

Hinz et al., "Polyglutamine Expansion Alters the Dynamics and Moleculare Architechur of Aggregates in Dentatorubropallidoluysian Atrophy", The Journal of Biological Chemistry (2012) vol. 287, No. 3, pp. 2068-2078.
Basso et al., "Mutant Copper-Zinc Superoxide Dismutase (SOD1) Induces Protein Secretion Pathway Alterations and Exosome Release in Astrocytes" The Journal of Biological Chemistry (2013) vol. 288, No. 22, pp. 15699-16711.
Guo et al., "Cell in Situ Structure of Neuronal C9orf72 Poly-GA Aggregates Reveals Proteasome Recruitment" CellPress (2018) 172: pp. 696-705.
Rabinovici et al., "Frontotemporal Lobar Degeneration: Epidemiology, Pathophysiology, Diagnosis and Management", CNS Drugs (2010) 24(5): pp. 375-398.
Saa et al., Biochemical detection of PrPTSE in blood-circulating exosomes by protein misfolding cyclic amplification (PMCA), Prion, vol. 7, Suppl. 1 (2013) pp. 19-20.
Guo et al., "In Situ Structure of Neuronal C9orf72 Poly-GA Aggregates Reveals Proteasome Recruitment" CellPress (2018) 172(4) pp. 696-705.
Outeiro et al., "Formation of Toxic Oligomeric a-Synucleain Species in Living Cells", PLoS One (2008) 3(4): e1867, pp. 1-9.
IPRP and Writtien Opinion Application No. PCT/GB2019/050599 dated Sep. 8, 2020.
Perez-Gonzalez et al., "The Exosome Secretory Pathway Transports Amyloid Precursor Protein Carboxy-terminal Fragments from the Cell into the Brain Extracellulare Space", Journal of Biological Chemistry (2012) vol. 287 pp. 43108-43115/.
McKhann et al., "The diagnosis of dementia due to Alzheimer's disease: Recommendationsl from the National Institute on Aging-Alzheimer's Association workgroups on diagnostic guidelines for Alzheimer's disease", Alzheimers Dement (2011) (3) pp. 263-269.
Van de Warrenburg et al., "EFNS/ENS Consensus on the diagnosis and management of chronic ataxias in adulthood", European Journal of Neurology (2014) 21: pp. 552-562.
Sangwan et al., "Atomic structure of a toxic, oligomeric segment of SOD1 linked to amyotrophic lateral sclerosis (ALS)", PNAS (2017) vol. 114, No. 33, pp. 8770-8775.
Alexander et al., "Validation of the new consensus criteria for the diagnosis of corticobasal degeneration", J. Neurol Neurosurg Psychiatry (2014) 85, pp. 923-927.
Traynor et al, "Clinical Features of Amyotrophic Lateral Sclerosis According to the E1 Excoral and Airlie House Diagnostic Criteria", ARCH Neurol, (2000) vol. 57, pp. 1171-1741.
Fitzpatrick et al., "Cryo-EM structures of Tau filaments from Alzheimer's disease brain", Nature (2017) 547 (7662) pp. 185-190.
Gallagher-Jones et al., "Sub-angstrom cryo-EM structure of a prion protofibril reveals a polar clasp", Nat Struct Mol Biol (2018) 25(2) pp. 131-134.
Gallea et al., "Structural Insights into Amyloid Oligomers of the Parkinson Disease-related Protein a-Synuclein" The Journal of Biological Chemistry (2014) vol. 39, pp. 26733-26742.
Hoglinger et al., "Clinical Diagnosis of Progressive Supranuclear Palsy: The Movement Disorder Society Criteria", Mov Disord. (2017) 32(6) pp. 853-864.
McKeith et al., "Diagnosis and management of dementia with Lewy bodies", Nerology (2017) 89: pp. 89-100.
Salvadores, et al., "Detection of Misfolded Ab Oligomers for Sensitive Biochemical Diagnosis of Alzheimer's Disease", Cell Report (2014) 7, pp. 261-268.
Schmidt et al., "Peptide dimer structure in an Ab(1-42) fibril visualized with cryo-EM", PNAS (2015) vol. 112, No. 38, pp. 11858-11863.
Böing et al., "Single-step isolation of extracellular vesicles by size-exclusion chromatography" Journal of Extracellulare Vesicles (2014) 3: 23430, pp. 1-11.
Danzer et al., "Exosomal cell-to-cell transmittion of alpha synuclein oligomers", (2012) 7:42, pp. 2-18.
Herva et al., Anti-amyloid Compounds Inhibit a-Synuclein Aggregation Induced by Protein Misfolding Cyclic Amplification (PMCA).
Luk et al., "Prospective diagnosis of sporadic CJD by the detection of abnormal PrP in patient urine", (2016) JAMA Neurol. 73(12): pp. 1454-1460.
Gonzalez-Montalban et al., "Highly Efficient Protein Misfolding Cyclic Amplification", PLoS Pathog 7(2): e1001277, pp. 1-10.
Zerr et al., "Clinical diagnosis and differential diagnosis of CJD and vCJD With special emphasis on laboratory test", APMIS (2002) 110, pp. 88-98.
Mollenhauer et al., "a-Synuclein and tau concentrations in cerebrospinal fluid of patients presenting with parkinsonism: a cohort study", Lancet Neurol (2011) 10, pp. 230-240.
Atarashi_et_al_"Ultrasensitive human prion detection in cerebrospinal fluid by real-time quaking-induced conversion." Nature Medicine, (2011) 17:2 pp. 175-178.
Tuttle et al., "Solid-State NMR Structure of a Pathogenic Fibril of Full-Lenth Human a-Synuclein" Nat Struct Mol Biol. (2016) 23(5) pp. 409-415.
Dubois et al., "Advancing research diagnostic criteria for Alzheimder's disease: the IWG-2 criteria" Lancet Neurol (2014) 13:pp. 614-629.
Andaloussi, et al., "Extracellular vesicles: biology and emerging therapeutic opportunities" Nature Reviews Drug Discover (2013 vol. 12, pp. 347-357.
Desai et al., "Diagnosis and treatment of Alzheimer's disease" Neurology (2005) 64/Suppl 3: S34-S39.
Kurzawa et al., "Glucocerebrosidase Mutations alter the endoplasmic reticulum and lysosomes in Lewy body disease", Journal of Neurochemistry, 123: 298-309 (2012).
Sidransky et al., "Multi-center analysis of glucocerebrosidase mutations in Parkinson disease", N. Engl. J. Med., 361(17): 1651-1661 (2009).
Nalls, et al., "A Multicenter Study of Glucocerebrosidase Mutations in Dementia with Lewy Bodies", JAMA Neurol., 70(6): 1-17 (2013).
Postuma et al., "MDS Clinical Diagnostic Criteria for Parkinson's Disease", Movement Disorders, 30(12): 1591-1599 (2015).
Kitatani et al., "The sphingolipid salvage pathway in ceramide metablism and signaling", Cell Signal., 20(6): 1010-1018 (2008).
Schueler et al., "Correlation between enzyme activity and substrate storage in a cell culture model system for Gaucher disease", J. Inherit. Metab. Dis., 27: 649-658 (2004).
Kim et al., "Diagnosis and differential diagnosis of MSA: boundary issues", J. Neurol., 262: 1801-1813 (2015).
Fu et al., "Phenotypic assays identify a small molecule modulator of the unfolded protein response with anti-diabetic activity", Sci. Transl. Med., 7(292): 1-28 (2015).
Gong et al., "Endoplasmic reticulum (ER) stress inhibitor salubrinal protects against ceramide-induced SH-SY5Y cell death", Biochemical and Biophysical Research Communications, 427: 461-465 (2012).
Sardi et al., "CNS expression of glucocerebrosidase corrected alpha-synuclein pathology and memory in a mouse model of Gaucher-related synucleinopathy", PNAS, 108(29): 12101-12106 (2011).
Atarashi et al., "Real-time quaking-induced conversion", Landes Bioscience, 5(3): 150-153 (2011).
Cooper et al., "Alpha-Synuclein Blocks ER-Golgi Traffic and Rab1 Rescues Neuron Loss in Parkinson's Models", Science, 313(5785): 324-328 (2006).
Goedert, "Alzheimer's and Parkinson's diseases: The prion concept in relation to assembled Aβ, tau and alpha-synuclein", Science, 349(6248): pp. 601 and 1255555-1 thru1255555-9 (2015).
Grey et al., "Acceleration of alpha-Synuclein Aggregation by Exosomes", The Journal of Biological Chemistry, 290(5):2969-2982 (2015).
Mousley et al., "Trans-Golgi Network and Endosome Dynamics Connect Ceramide Homeostasis with Regulation of the Unfolded Protein Response and TOR Signaling in Yeast", Molecular Biology of the Cell, 19:4785-4803 (2008).

(56) References Cited

OTHER PUBLICATIONS

Ngolab et al., "Brain-derived exosomes from dementia with Lewy bodies propagate alpha-synuclein pathology", Acta Neuropathologica Communications, 5: 46 (2017).
Ron et al., "ER retention and degradation as the molecular basis underlying Gaucher disease heterogeneity", Human Molecular Genetics, 14(16): 2387-2398 (2005).
Invitation to Pay Additional Fees for International PCT Application No. PCT/GB2019/050599 dated Apr. 16, 2019.
Japanese Office Action Issued for Japanese Patent Application No. 2020-546431 dated Jul. 25, 2022 with English Translation.
Japanese Office Action for Japanese Patent Application No. 2020-546431 with English Translation (dated Feb. 6, 2023).
Examination Report for Canadian Application No. 3,092,184, dated Oct. 24, 2023.

1. Particle size and concentration     ▨ M04-07

Tunable Resistive Pulse Sensing (TRPS)

2. Particle imaging

Transmission electron microscopy

DETECTION OF PATHOLOGICAL PROTEIN AGGREGATION

The present invention provides novel methods of identifying, monitoring or determining the risk of developing a protein misfolding neurodegenerative disorder in a subject, particularly an alpha synucleinopathy (including Parkinson's disease and dementia with Lewy bodies) using extracellular vesicle samples. Corresponding methods for selecting a treatment and assaying for the presence of a pathological prion-like protein (or one or more ceramide species) in an extracellular vesicle sample are also provided.

BACKGROUND

A large number of neurodegenerative disorders are associated with misfolding, aggregation and tissue accumulation of proteins. These disorders, termed "protein misfolding neurodegenerative disorders" herein, include Parkinson's disease, Dementia with Lewy Bodies, Multiple System Atrophy, Creutzfeldt-Jakob disease, Alzheimer's disease, tauopathies (such as Alzheimer's disease, frontotemporal lobar degeneration, progressive supranuclear palsy and corticobasal degeneration), Huntington's disease, Motor Neurone disease, dentatopallidorubroluysian atrophy, spinocerebellar ataxia, and many others (Salvadores et al., 2014).

Identification of affected individuals at early stages of disease prior to display of clinical symptoms is generally problematic. This is because there is a lack of widely accepted, reliable, sensitive and objective molecular diagnostic methods for identifying, monitoring and evaluating the risk of developing protein misfolding neurodegenerative disorders. Diagnosis of such diseases therefore relies heavily on neurological and neuropsychiatric evaluation, which typically only becomes diagnostic at later stages of disease development.

As an example, Parkinson's disease is a condition in which parts of the brain become progressively damaged over many years. The main symptoms of Parkinson's disease are involuntary shaking of particular parts of the body (tremor), slow movement and inflexible muscles. A person with Parkinson's disease can also experience a wide range of other physical and psychological symptoms including depression and anxiety, balance problems, loss of sense of smell (anosmia), problems sleeping (insomnia) and memory problems.

Additionally, there are two types of dementia related to Parkinson's; Parkinson's dementia and dementia with Lewy bodies. When the motor symptoms of Parkinson's are present for at least a year before experiencing dementia, this is known as Parkinson's dementia. Dementia with Lewy bodies is diagnosed when the symptoms of dementia appear before or at the same time as Parkinson's symptoms. People with Parkinson's tend to have greater impairment of attention, orientation in and negotiation of environment. They are also less flexible in their way of thinking.

Currently, diagnosis is made based on a patient's symptoms, medical history and detailed physical examination. Early stage Parkinson's is particularly difficult to diagnose as the symptoms are usually mild. At present, full clinical diagnosis is established in highly specialised clinical settings and is based on neuropsychological and neuroradiological assessments. This usually requires repeated attendance to specialist services, which delays the diagnosis and thus initiation of treatments and support by months. There is currently no cure for Parkinson's, but there are lots of different treatments, therapies and support available to help manage the condition.

1 in 500 people are affected by Parkinson's disease, meaning that there are an estimated 127,000 people in the UK with the condition. Most people with Parkinson's start to develop symptoms when they're over 50, although around 1 in 20 people with the condition first experience symptoms when they're under 40. Men are slightly more likely to get Parkinson's disease than women. A study by the UN reports that 1.8 billion people will be over 60 by 2050 projecting 18,000,000 potential new patients.

In the United States, at least 500,000 people are believed to suffer from Parkinson's with around 50,000 new cases reported each year. Parkinson's is calculated to cost $14.4 billion a year, with indirect costs (e.g., reduced employment) conservatively estimated at $6.3 billion (or close to $10,000 per person). These costs are predicted to double by 2040. In the UK the cost is estimated to be between £0.4 and £3.3 billion a year. Research shows that the cost of Parkinson's could be significantly reduced through improvements in early diagnosis which would help planning, avoidance of future admissions and improved clinical management.

At a molecular level, alpha-synuclein aggregation is known to play a central role in Parkinson's (PD), dementia with Lewy Bodies (DLB) and Multiple System Atrophy (MSA) disease pathology. Alpha-synuclein is a 140 amino acid long protein that has been detected within and on the outside of exosomes and other extracellular vesicles (reviewed in Loov et al., 2016). Despite many studies showing a change in alpha-synuclein levels in patients with Parkinson's disease (e.g. a slight reduction in alpha-synuclein level in cerebrospinal fluid (CSF) samples), the data from different studies is not consistent. In addition, standardisation of methods for measuring alpha-synuclein between laboratories has proven difficult. Accordingly, using the currently available methodology, the total amount of alpha-synuclein present within a biological sample of a subject (including extracellular vesicle samples) does not appear to be a reliable biomarker of disease.

In its pathological state, alpha synuclein loses its native structure. Conformationally altered alpha-synuclein may initiate the formation of dimers and trimers, subsequently forming soluble oligomers and protofibrils and deposit as fibrils and mature as aggregates.

Recently, exosomes have been implicated in the dissemination of misfolded proteins in a variety of neurodegenerative disorders, including Parkinson's disease. For example, extracellular alpha-synuclein was recently implied in the prion-like transmission of pathological alpha-synuclein from diseased to healthy neurons where misfolded alpha-synuclein might serve as a seed to induce the aggregation of soluble alpha-synuclein.

A recently described technique called real-time quaking-induced conversion (RT-QuIC) exploits the ability of prion protein to induce self-aggregation and has recently been used to detect pathological alpha synuclein in CSF samples from DLB and Parkinson's disease patients (Fairfoul et al., 2016). An alternative method has also recently been developed ("protein misfolding cyclic amplification (PMCA)") to detect the presence of alpha synuclein aggregation (Herva et al., 2014). Although these methods show promise, the time taken to complete each assay is long, and the samples needed for analysis (CSF or brain homogenate) require invasive procedures, limiting their application to patients with a high index of suspicion of disease (e.g. patients in the late stages of disease progression with several clinical symptoms and indicators of disease).

There is a need for improved diagnostic tools for early stage protein misfolding neurodegenerative disorders such as PD or DLB.

BRIEF SUMMARY OF THE DISCLOSURE

The inventors have now surprisingly found that the presence of pathological alpha-synuclein in extracellular vesicle samples from patients with PD or DLB can be used as a reliable marker for identifying or monitoring disease, and importantly the risk of developing disease in a person who does not yet show clinical symptoms. In addition, they have demonstrated that the lipid composition of extracellular vesicles obtained from PD and DLB patients is significantly different to that of controls (particularly the ceramide composition of the extracellular vesicles). The inventors have therefore provided a novel means for detecting, monitoring and diagnosing disease.

The inventors have used size exclusion chromatography (SEC) to obtain the extracellular vesicle (EV) samples that are used for subsequent detection of pathological alpha synuclein. Use of SEC is advantageous as it is a very gentle means for enriching for EVs based on the size of the vesicles and not density, with no risk of protein complex formation, and vesicle aggregation and enrichment in other lipids present in the sample (reviewed in Boing et al., 2014). However, the invention applies equally to EV samples obtained by other methods, examples of which are described in more detail below.

The inventors have detected the presence of pathological alpha synuclein in EVs by exploiting its ability to induce self-aggregation. They have shown that known methods for detecting pathological alpha synuclein can be used to assay EV samples to provide more rapid and more sensitive assay protocols. By way of example, the inventors have identified that the time required for detection of pathological alpha synuclein in a patient sample using a known method, RT-QuIC, can be reduced from approximately 120 hours (current length of the assay) to 48-80 hours when isolated EVs are used (without any further optimisation of the method). Further refinement of the assay would allow a more rapid assay method.

Although the invention has been exemplified using RT-QuIC as a means for detecting pathological alpha synuclein, any other suitable method for detection of pathological alpha synuclein may also be used. By way of an alternative non-limiting example, PMCA may also be used (Herva et al., 2014).

The inventors have shown that EV samples obtained from several different biological samples (including samples previously shown to be unsuitable for detection of pathological alpha synuclein) can reliably be used for detecting, monitoring and identifying disease (or risk of disease). Advantageously, biological samples that may be obtained by low-invasive, or non-invasive means (such as blood, urine or saliva) may now be used as a source of EVs for detecting pathological alpha synuclein. The inventors have therefore developed a more sensitive means for detecting, monitoring and identifying disease (or risk of disease).

Furthermore, the inventors have shown that detection of pathological alpha synuclein can be used to detect prodromal alpha synucleinopathy, even before clinical symptoms occur. The methods described herein therefore can be used to detect, monitor and identify early stages of disease (or risk of disease). They therefore provide a more sensitive means for detecting disease features for early clinical assessment of patients with alpha-synucleinopathies such as Parkinson's disease or DLB.

The invention has been exemplified by detecting pathological alpha synuclein in EV samples obtained from PD and DLB patients. However, the invention applies equally to the detection of other pathological prion-like proteins, which also aggregate (e.g. into oligomers and fibrils) when in a pathological state. Advantageously, the presence of each of these prion-like pathological proteins can be detected by exploiting their ability to induce self-aggregation (and thus methods such as RT-QuIC and PMCA (or modified versions thereof) may be used for their detection).

The inventors have also identified that EVs obtained from PD or DLB patient CSF samples display significant lipid changes compared to control. These data suggest that significant lipid changes in the EVs of patients are crucial in disease state. Without being bound to a particular theory, it is thought that these lipid changes constitute part of the high sensitivity and specificity of the methods for detecting pathological alpha synuclein described herein as the alpha synuclein aggregation assay may be responsive to both alterations—the change in ceramide composition and the ability to induce synuclein folding. The changes in ceramides in the disease state are very significant and similar to changes that are observed in the patient's brain tissue (both for DLB and Parkinson's patients; data unpublished). Advantageously, the changes in lipid composition can be used as a biomarker for detecting, monitoring and identifying disease (or risk of disease), particularly in respect of alpha synucleinopathies, more particularly in respect of PD and/or DLB.

In one aspect, the invention provides an in vitro method of identifying or monitoring a protein misfolding neurodegenerative disorder in a subject, comprising assaying an extracellular vesicle sample from the subject for the presence of a pathological prion-like protein, wherein the presence of a pathological prion-like protein is indicative of the protein misfolding neurodegenerative disorder. Optionally, the protein misfolding neurodegenerative disorder is alpha synucleinopathy and the pathological prion-like protein is alpha-synuclein.

In another aspect, the invention provides an in vitro method of determining the risk of a subject developing a protein misfolding neurodegenerative disorder, comprising assaying an extracellular vesicle sample from the subject for the presence of a pathological prion-like protein, wherein the presence of a pathological prion-like protein is indicative of an increased risk of the subject developing a protein misfolding neurodegenerative disorder. Optionally, the protein misfolding neurodegenerative disorder is alpha synucleinopathy and the pathological prion-like protein is alpha-synuclein.

In another aspect, the invention provides in vitro method of determining the presence of a pathological prion-like protein in a subject suspected of having a protein misfolding neurodegenerative disorder or having an increased risk of developing a protein misfolding neurodegenerative disorder, the method comprising:
  (a) providing an extracellular vesicle sample from the subject; and
  (b) determining the presence of a pathological prion-like protein in the extracellular vesicle sample. Optionally, the protein misfolding neurodegenerative disorder is alpha synucleinopathy and the pathological prion-like protein is alpha-synuclein.

In another aspect, the invention provides an in vitro method of selecting a treatment for a subject having a disease, comprising determining the presence of a pathological prion-like protein in an extracellular vesicle sample from the subject, wherein the presence of a pathological prion-like protein indicates that the subject would benefit from treatment for a protein misfolding neurodegenerative disorder. Optionally, the protein misfolding neurodegenerative disorder is alpha synucleinopathy and the pathological prion-like protein is alpha-synuclein.

Suitably;
a) the protein misfolding neurodegenerative disorder is an alpha synucleinopathy selected from the group consisting of Parkinson's disease, Dementia with Lewy Bodies and Multiple System Atrophy; and the pathological prion-like protein is pathological alpha-synuclein;
b) the protein misfolding neurodegenerative disorder is Creutzfeldt-Jakob disease; and the pathological prion-like protein is prion protein;
c) the protein misfolding neurodegenerative disorder is Alzheimer's disease; and the pathological prion-like protein is pathological amyloid beta;
d) the protein misfolding neurodegenerative disorder is a tauopathy selected from the group consisting of Alzheimer's disease, frontotemporal Lobar degeneration, progressive supranuclear palsy and corticobasal degeneration; and the pathological prion-like protein is pathological tau protein;
e) the protein misfolding neurodegenerative disorder is Huntington's disease; and the pathological prion-like protein is pathological huntingtin protein;
f) the protein misfolding neurodegenerative disorder is Motor Neurone disease; and the pathological prion-like protein is selected from the group consisting of pathological superoxide dismutase, c9orf72, and valosin and other prion-like proteins associated with Motor Neurone disease;
g) the protein misfolding neurodegenerative disorder is a dentatopallidorubroluysian atrophy; and the pathological prion-like protein is pathological atrophin protein; or
h) the protein misfolding neurodegenerative disorder is a spinocerebellar ataxia; and the pathological prion-like protein is pathological ataxin, optionally wherein the pathological ataxin is selected from the group consisting of ataxin-1, ataxin-2 and ataxin-3.

Suitably, the subject is human.

Suitably, the subject has, or is suspected of having, a protein misfolding neurodegenerative disorder. Optionally, the protein misfolding neurodegenerative disorder is alpha synucleinopathy.

Suitably, the subject has a protein misfolding neurodegenerative disorder. Optionally, the protein misfolding neurodegenerative disorder is alpha synucleinopathy.

Suitably, the subject has an early stage protein misfolding neurodegenerative disorder. Optionally, the protein misfolding neurodegenerative disorder is alpha synucleinopathy.

Suitably, the extracellular vesicle sample is obtained from a biological sample selected from CSF, blood, brain tissue homogenate, urine, saliva or a combination thereof.

Suitably, the blood sample is selected from the group consisting of plasma, serum, platelets and buffy coats.

Suitably, the extracellular vesicle sample is obtained using size exclusion chromatography.

Suitably, the method further comprises the steps of:
i) providing a biological sample from the subject; and
ii) obtaining an extracellular vesicle sample from the biological sample using size exclusion chromatography.

Suitably, the presence of the pathological prion-like protein is detected using RT-QuIC or PMCA. Optionally, the pathological prion-like protein is alpha synuclein.

In another aspect, the invention provides the use of an in vitro extracellular vesicle sample for identification or monitoring of a protein misfolding neurodegenerative disorder in a subject, or for determining the risk of developing a protein misfolding neurodegenerative disorder in a subject. Optionally, the protein misfolding neurodegenerative disorder is alpha synucleinopathy.

Suitably, the use comprises any of the features described herein.

In another aspect, the invention provides an in vitro method of identifying or monitoring an alpha synucleinopathy in a subject, comprising:
a) assessing the amount of at least one ceramide species selected from the group consisting of Cer 32:1, Cer 33:1, Cer 34:1, Cer 34:2, Cer37:1, Cer 38:1, Cer 38:2, Cer 39:1, Cer 39:2, Cer 40:1, Cer 40:2, Cer 41:1, Cer 41:2, Cer 40:1(OH) and Cer 40:2(OH) in an extracellular vesicle sample of the subject; and
b) comparing the assessed amount of the at least one ceramide species with a reference value for the at least one ceramide species;
wherein an assessed amount of the at least one ceramide species greater than the reference value for the at least one ceramide species is indicative of an alpha synucleinopathy.

In another aspect, the invention provides an in vitro method of determining the risk of a subject developing an alpha synucleinopathy, comprising:
a) assessing the amount of at least one ceramide species selected from the group consisting of Cer 32:1, Cer 33:1, Cer 34:1, Cer 34:2, Cer37:1, Cer 38:1, Cer 38:2, Cer 39:1, Cer 39:2, Cer 40:1, Cer 40:2, Cer 41:1, Cer 41:2, Cer 40:1(OH) and Cer 40:2(OH) in an extracellular vesicle sample of the subject; and
b) comparing the assessed amount of the at least one ceramide species with a reference value for the at least one ceramide species;
wherein an assessed amount of the at least one ceramide species greater than the reference value for the at least one ceramide species is indicative of an increased risk of the subject developing an alpha synucleinopathy.

In another aspect, the invention provides an in vitro method of assessing the amount of at least one ceramide species selected from the group consisting of Cer 32:1, Cer 33:1, Cer 34:1, Cer 34:2, Cer37:1, Cer 38:1, Cer 38:2, Cer 39:1, Cer 39:2, Cer 40:1, Cer 40:2, Cer 41:1, Cer 41:2, Cer 40:1(OH) and Cer 40:2(OH) in a subject suspected of having an alpha synucleinopathy or having an increased risk of developing an alpha synucleinopathy, the method comprising:
(a) providing an extracellular vesicle sample from the subject; and
(b) assessing the amount of at least one ceramide species selected from the group consisting of Cer 32:1, Cer 33:1, Cer 34:1, Cer 34:2, Cer37:1, Cer 38:1, Cer 38:2, Cer 39:1, Cer 39:2, Cer 40:1, Cer 40:2, Cer 41:1, Cer 41:2, Cer 40:1(OH) and Cer 40:2(OH) in the extracellular vesicle sample.

In another aspect, the invention provides an in vitro method of selecting a treatment for a subject having a disease, comprising:
  a) assessing the amount of at least one ceramide species selected from the group consisting of Cer 32:1, Cer 33:1, Cer 34:1, Cer 34:2, Cer37:1, Cer 38:1, Cer 38:2, Cer 39:1, Cer 39:2, Cer 40:1, Cer 40:2, Cer 41:1, Cer 41:2, Cer 40:1(OH) and Cer 40:2(OH) in an extracellular vesicle sample of the subject; and
  b) comparing the assessed amount of the at least one ceramide species with a reference value for the at least one ceramide species;
  wherein an assessed amount of the at least one ceramide species greater than the reference value for the at least one ceramide species indicates that the subject would benefit from treatment for an alpha synucleinopathy.

Suitably, the alpha synucleinopathy is selected from the group consisting of Parkinson's disease, Dementia with Lewy Bodies and Multiple System Atrophy.

Suitably, the subject is human.

Suitably, the subject has, or is suspected of having, an alpha synucleinopathy.

Suitably, the subject has an alpha synucleinopathy.

Suitably, the subject has an early stage alpha synucleinopathy.

Suitably, the extracellular vesicle sample is obtained from a biological sample selected from CSF, blood, brain tissue homogenate, urine, saliva or a combination thereof.

Suitably, the blood sample is selected from the group consisting of plasma, serum, platelets and buffy coats.

Suitably, the extracellular vesicle sample is obtained using size exclusion chromatography.

Suitably, the method further comprises the steps of:
  i) providing a biological sample from the subject; and
  ii) obtaining an extracellular vesicle sample from the biological sample using size exclusion chromatography.

Suitably, the reference value is obtained from a control sample or is a pre-determined reference value.

In another aspect, the invention provides for the use of at least one extracellular vesicle ceramide species selected from the group consisting of Cer 32:1, Cer 33:1, Cer 34:1, Cer 34:2, Cer37:1, Cer 38:1, Cer 38:2, Cer 39:1, Cer 39:2, Cer 40:1, Cer 40:2, Cer 41:1, Cer 41:2, Cer 40:1(OH) and Cer 40:2(OH) for identification or monitoring of an alpha synucleinopathy in a subject, or for determining the risk of developing an alpha synucleinopathy in a subject.

Suitably, the use comprises any of the features described herein.

Throughout the description and claims of this specification, the words "comprise" and "contain" and variations of them mean "including but not limited to", and they are not intended to (and do not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

Various aspects of the invention are described in further detail below.

BRIEF DESCRIPTION OF THE DRAWINGS

Embodiments of the invention are further described hereinafter with reference to the accompanying drawings, in which.

DETAILED DESCRIPTION

Figure 1:
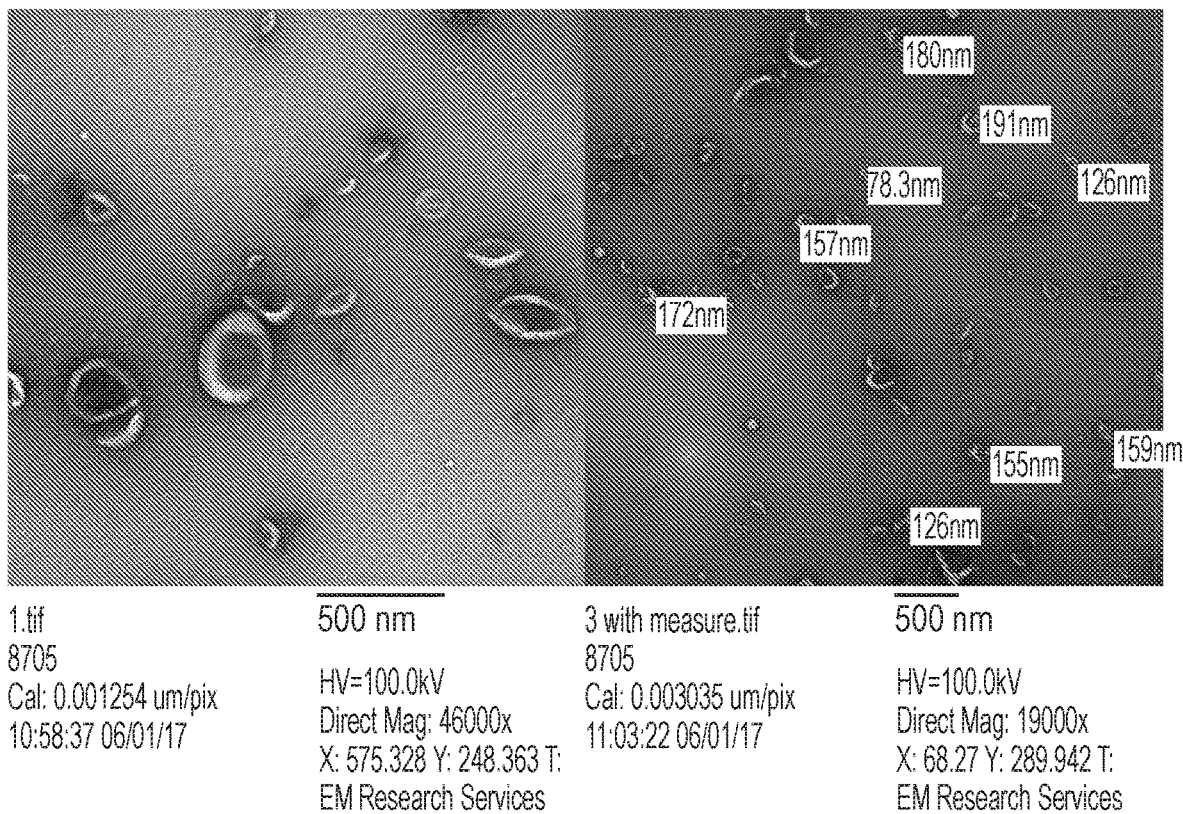
FIG. 1 shows representative electron microscopy images of extracellular vesicles purified from post-mortem CSF.

The inventors have now surprisingly found that the presence of pathological alpha-synuclein in extracellular vesicle samples from patients with PD or DLB can be used as a reliable marker for identifying or monitoring disease (or risk of developing disease). In addition, they have demonstrated that the lipid composition of extracellular vesicles obtained from PD and DLB patients is significantly different to that of controls (particularly the ceramide composition of the extracellular vesicle membranes). The inventors have therefore provided novel means for detecting, monitoring and diagnosing disease.

An in vitro method of identifying or monitoring a protein misfolding neurodegenerative disorder in a subject is provided herein, comprising assaying an extracellular vesicle sample from the subject for the presence of a pathological prion-like protein, wherein the presence of a pathological prion-like protein is indicative of the protein misfolding neurodegenerative disorder.

It is clear to a person of skill in the art that the specific pathological prion-like protein that is present in the EV sample identifies the specific (i.e. corresponding) protein misfolding neurodegenerative disorder. The link between the pathological prion-like protein and its corresponding protein misfolding neurodegenerative disorder is well known in the art. As an example, when the specific pathological prion-like protein that is present in the EV sample is alpha-synuclein, this identifies the specific (i.e. corresponding) protein misfolding neurodegenerative disorder to be an alpha-synucleinopathy such as Parkinson's disease, or dementia with Lewy bodies. Other examples of specific pathological prion-like proteins and their corresponding protein misfolding neurodegenerative disorder are given throughout the application. This applies to all embodiments described herein.

An in vitro method of determining the risk of a subject developing a protein misfolding neurodegenerative disorder is also provided herein, comprising assaying an extracellular vesicle sample from the subject for the presence of a pathological prion-like protein, wherein the presence of a pathological prion-like protein is indicative of an increased risk of the subject developing a protein misfolding neurodegenerative disorder.

The identification of a protein misfolding neurodegenerative disorder in a subject from analysis of a suitable sample equates with diagnosis of the condition, particularly when carried out in conjunction with other diagnostic methods such as clinical evaluation of symptoms and/or neurophysical evaluation of the subject. The phrases "identification of a protein misfolding neurodegenerative disorder" (or equivalent) and "diagnosis of a protein misfolding neurodegenerative disorder" (or equivalent) are therefore used interchangeably herein.

Monitoring of a protein misfolding neurodegenerative disorder in a subject over time assists in the earliest possible identification of disease progression (e.g. a worsening in disease status or disease symptoms) or of an improvement in disease status or symptoms (e.g. over a treatment period). Such monitoring naturally involves the taking of repeated samples over time. The method may therefore be repeated at one or more time intervals for a particular subject and the results compared to monitor the development, progression or improvement in the protein misfolding neurodegenerative disorder of that subject over time, wherein a change in the amount of pathological prion-like protein in an EV sample of the subject is indicative of a change in the progression of the protein misfolding neurodegenerative disorder in the subject.

Disease progression over time may be indicated by an increase in the amount of pathological prion-like protein detected when the results of two or more time intervals are compared. In other words, if the method is performed a plurality of times, disease progression may be indicated when the amount of pathological prion-like protein detected at the later time interval(s) is higher than that detected at the earlier time interval(s). An "increase" in the amount of pathological prion-like protein encompasses detection of the pathological prion-like protein at a later time interval when no pathological prion-like protein was detected (i.e. it was not present at detectable levels) when the method was performed previously (i.e. at an earlier time interval) on the same subject (and an equivalent EV sample type).

Suitable time intervals for monitoring disease progression can easily be identified by a person of skill in the art and will depend on the specific protein misfolding neurodegenerative disorder being monitored. As a non-limiting example, the method may be repeated at least every six months, or at least every year, or at least every two years when monitoring the progression of Parkinson's disease.

An improvement in disease status or symptoms (e.g. over a treatment period) may be indicated by a decrease in the amount of pathological prion-like protein detected when the results of two or more time intervals are compared. In other words, if the method is performed a plurality of times, an improvement in disease status may be indicated when the amount of pathological prion-like protein detected at the later time interval(s) is lower (i.e. decreased) than that detected at the earlier time interval(s). A "decrease" in the amount of pathological prion-like protein therefore also encompasses detection of the pathological prion-like protein at an early time interval followed by a repeat of the method at a later time interval wherein no pathological prion-like protein was detected (i.e. the prion-like protein was undetectable or absent at the later time interval) for the same subject (and an equivalent EV sample type).

An improvement in disease status or symptoms (e.g. over a treatment period) may also be indicated by a slowed increase in pathological prion-like protein over time or stabilised levels of pathological prion-like protein over time (compared to the level of pathological prion-like protein observed in the absence of treatment over the equivalent time period, or compared to equivalent controls).

Suitable time intervals for monitoring an improvement in disease status or symptoms (e.g. during treatment of the subject) can easily be identified by a person of skill in the art and will depend on the specific protein misfolding neurodegenerative disorder being monitored. As a non-limiting example, the method may be repeated at least every six months, or at least every year, or at least every two years when monitoring Parkinson's Disease (e.g. during treatment of the subject for Parkinson's disease.

Determining the risk of a subject developing a protein misfolding neurodegenerative disorder assists in the earliest possible identification of disease. This allows for early intervention and/or commencement of treatment at earlier stages of disease progression. It also provides a means for monitoring high risk individuals (i.e. individuals that are very likely or more likely to develop the disease) such that treatment or preventative measures may be put in place at the earliest opportunity. In this context, the inventors have shown that the methods described herein can be used to successfully detect prodromal alpha synucleinopathy, even before clinical symptoms occur. The methods described herein therefore can be used to detect, monitor and identify early stages of disease (or risk of disease). They therefore provide a more sensitive means for detecting disease features for early clinical assessment of patients with alpha-synucleinopathies such as Parkinson's disease.

The methods described herein provide a novel means for identifying or monitoring a protein misfolding neurodegenerative disorder in a subject, or determining the risk of a subject developing a protein misfolding neurodegenerative disorder.

As used herein, "protein misfolding disorder" refers to a class of disorders (also known as the proteinopathies, proteopathies, protein conformational disorders or protein misfolding diseases) wherein specific proteins become structurally abnormal, and thereby disrupt the function of cells, tissues and organs of the body. Typically, these pathological proteins fail to fold into their normal configuration, and in this misfolded state, the proteins can become toxic in some way (a gain of toxic function) or lose their normal function.

As used herein, "protein misfolding neurodegenerative disorder" refers to a subset of protein misfolding disorders that are associated with degeneration of the nervous system, especially the neurons in the brain. This group of disorders include Parkinson's disease (including Parkinson's disease dementia), dementia with Lewy bodies, Multiple System Atrophy, Creutzfeldt-Jakob disease, Alzheimer's disease, tauopathies (such as Alzheimer's disease, frontotemporal lobar degeneration, progressive supranuclear palsy and corticobasal degeneration), Huntington's disease, Motor Neurone disease, dentatopallidorubroluysian atrophy, spinocerebellar ataxia, and many others (Salvadores et al., 2014). For each of these protein misfolding neurodegenerative disorders, a specific pathological prion-like protein has been identified to play a central role in disease.

For example, for protein misfolding neurodegenerative disorders that are alpha synucleinopathies (e.g. Parkinson's disease (including Parkinson's disease dementia), dementia with Lewy bodies and Multiple System Atrophy) the pathological prion-like protein is pathological alpha-synuclein, which in humans can be identified using NCBI GenBank or UniProt (Gene ID: 6622; Protein ID: P37840).

The synucleinopathies are a set of neurodegenerative disorders associated with the deposition of fibrillary aggregates of alpha-synuclein within selective populations of neurons and glia. These deposits can be found within neuronal soma such as Lewy bodies (LB) or in dystrophic neurites in diseases such as Parkinson's disease (PD) or dementia with Lewy Bodies (DLB) or in glial cytoplasmic inclusions in multiple system atrophy (MSA). Synucleinopathies such as Parkinson's disease, dementia with Lewy bodies and multiple system atrophy are clinically well defined, details of which can be found in the following references: for DLB—McKeith et al. 2017; for PD—Postuma et al. 2015; for MSA—Kim et al. 2015.

As used herein, "pathological alpha synuclein" refers to alpha synuclein protein having an abnormal structural conformation, as described in Gallea et al. 2014 and Tuttle et al. 2016. As described elsewhere herein, pathological alpha synuclein is prone to aggregate into beta-sheet fibrils and may initiate formation of dimers and trimers, subsequently forming soluble oligomers and protofibril that deposit as fibrils and mature as aggregates. Pathological alpha synuclein can therefore be detected directly by the presence of alpha synuclein aggregates/alpha synuclein aggregation. Several methods for detecting aggregation of these proteins are well known including immunoEM, RT-QuIC and PMCA.

As a further example, when the protein misfolding neurodegenerative disorder is Creutzfeldt-Jakob disease, the pathological prion-like protein is pathological prion protein, which in humans can be identified using NCBI GenBank or UniProt (Gene ID: 5621; Protein ID: P04156). As used herein, "pathological prion protein" refers to a prion protein having an abnormal structural conformation, as described in Gallagher-Jones M et al. 2018. Pathological prion protein misfolds into a self-propagating conformation with the tendency to aggregate and form infectious prions. Pathological prion protein can therefore be detected directly by the presence of prion protein aggregates/prion protein aggregation. Several methods for detecting aggregation of these proteins are well known including immunoEM, RT-QuIC and PMCA.

Creutzfeldt-Jakob disease is clinically well defined, details of which can be found in Zerr et al. 2002.

As a further example, when the protein misfolding neurodegenerative disorder is Alzheimer's disease, the pathological prion-like protein is pathological amyloid beta, which in humans can be identified using NCBI GenBank or UniProt (Gene ID: 351; Protein ID: P05067). As used herein, "pathological amyloid beta" or "Aβ" refers to peptides of 36-43 amino acids that are the main component of the amyloid plaques found in the brains of Alzheimers patients. The peptides derive from the amyloid precursor protein (APP), which is cleaved by beta secretase and gamma secretase to yield Aβ. Aβ molecules can aggregate to form flexible soluble oligomers which are toxic to nerve cells. The structure of amyloid beta is described in Schmidt et al. 2015. Aβ can be detected directly by the presence of Aβ aggregates/Aβ aggregation. Several methods for detecting aggregation of these proteins are well known including immunoEM, RT-QuIC and PMCA.

Alzheimer's disease is clinically well defined, details of which can be found in Desai et al. 2005; McKhann et al. 2011; and Dubois et al. 2014.

As a further example, when the protein misfolding neurodegenerative disorder is a tauopathy (for example Alzheimer's disease, frontotemporal Lobar degeneration, progressive supranuclear palsy or corticobasal degeneration), the pathological prion-like protein is pathological tau protein, which in humans can be identified using NCBI GenBank or UniProt (Gene ID: 4137; Protein ID: P10636). As used herein, "pathological tau protein" refers to tau protein having an abnormal structural conformation, as described in Fitzpatrick et al. 2017. Pathological tau protein misfolds into a self-propagating conformation with the tendency to aggregate. Pathological tau protein can therefore be detected directly by the presence of tau protein aggregates/tau protein aggregation. Several methods for detecting aggregation of these proteins are well known including immunoEM, RT-QuIC and PMCA.

Tauopathies such as Alzheimer's disease, frontotemporal Lobar degeneration, progressive supranuclear palsy or corticobasal degeneration are clinically well defined, details of which can be found in for example Hoglinger G U et al. 2017; Gil et al., 2010 (for frontotemporal Lobar degeneration) and Alexander et al., 2014 (for corticobasal degeneration).

As a further example, when the protein misfolding neurodegenerative disorder is Huntington's disease, the pathological prion-like protein is pathological huntingtin protein, which in humans can be identified using NCBI GenBank or UniProt (Gene ID: 3064; Protein ID: P42858). As used herein, "pathological huntingtin protein" refers to huntingtin protein having an abnormal structural conformation that is generated due to an expanded, unstable trinucleotide repeat in the huntingtin gene, which translates as a polyglutamine repeat in the protein product (as described in Isas et al., 2017). Pathological huntingtin protein misfolds into a self-propagating conformation with the tendency to aggregate. Pathological huntingtin protein can be detected directly by the presence of huntingtin protein aggregates/huntingtin protein aggregation. Several methods for detecting aggregation of these proteins are well known including immunoEM.

Huntington's disease is clinically well defined, details of which are well known to a person of skill in the art (see for example Pagan et al., 2017).

As a further example, when the protein misfolding neurodegenerative disorder is Motor Neurone disease, the pathological prion-like protein is selected from the group consisting of pathological superoxide dismutase (SOD1), c9orf72, and valosin, which in humans can be identified using NCBI GenBank or UniProt ID numbers as follows: SOD1 (Gene ID: 6647, Protein ID: P00441); c9orf72 (Gene ID: 203228, Protein ID: Q96LT7); valosin (Gene ID: 7415, Protein ID: P55072). As used herein, "pathological superoxide dismutase, c9orf72, and valosin" refers to superoxide dismutase, c9orf72, and valosin having an abnormal structural conformation which is described in the following references: SOD1: Sangwan et al. 2017; c9orf72: Guo et al. 2018; and valosin: Basso et al. 2013. Pathological superoxide dismutase, c9orf72, and valosin misfold into a self-propagating conformation with the tendency to aggregate. Pathological superoxide dismutase, c9orf72, and valosin protein can be detected directly by the presence of superoxide dismutase, c9orf72, and valosin protein aggregates/superoxide dismutase, c9orf72, and valosin protein aggregation. Other rare forms of Motor Neurone Disease are caused by aggregation of other prion-like proteins known to those who are skilled in the art. Several methods for detecting aggregation of these proteins are well known including immunoEM.

Motor Neurone disease is clinically well defined, details of which are well known to a person of skill in the art (see for example Traynor et al., 2000).

As a further example, when the protein misfolding neurodegenerative disorder is dentatopallidorubroluysian atrophy, the pathological prion-like protein is pathological atrophin protein, which in humans can be identified using NCBI GenBank or UniProt (Gene ID: 1822, Protein ID: P54259). As used herein, "pathological atrophin protein" refers to atrophin protein having an abnormal structural conformation which is described in Hinz et al. 2012. Pathological atrophin protein misfolds into a self-propagating conformation with the tendency to aggregate. Pathological atrophin protein can be detected directly by the presence of atrophin protein aggregates/atrophin protein aggregation. Several methods for detecting aggregation of these proteins are well known including immunoEM.

Dentatopallidorubroluysian atrophy is clinically well defined, details of which are well known to a person of skill in the art (see for example Wardle et al., 2009).

As a further example, when the protein misfolding neurodegenerative disorder is spinocerebellar ataxia, the pathological prion-like protein is pathological ataxin such as ataxin-1, ataxin-2 and ataxin-3, which in humans can be identified using NCBI GenBank or Uniprot (for ataxin 1 (Gene ID: 6310, ProteinID: P54253); for ataxin 2 (Gene ID: 6311, Protein ID: Q99700); for ataxin 3 (Gene ID: 4287, Protein ID: P54252). As used herein, "pathological ataxin" refers to ataxin protein having an abnormal structural conformation which is described in Ruggeri et al. 2015. Pathological ataxin protein misfolds into a self-propagating conformation with the tendency to aggregate. Pathological ataxin protein can be detected directly by the presence of ataxin protein aggregates/ataxin protein aggregation. Several methods for detecting aggregation of these proteins are well known including immunoEM.

Spinocerebellar ataxia is clinically well defined, details of which are well known to a person of skill in the art (see for example van de Warrenburg et al., 2014).

The term "subject" as used herein refers to a mammal. A subject therefore refers to, for example, dogs, cats, horses, cows, pigs, guinea pigs, and the like. The subject can be a human. When the subject is a human, the subject may be referred to herein as a patient. The terms "subject", "individual", and "patient" are used herein interchangeably.

The subject can be symptomatic (e.g., the subject presents symptoms associated with a protein misfolding neurodegenerative disorder), or the subject can be asymptomatic (e.g., the subject does not present symptoms associated with a protein misfolding neurodegenerative disorder but may show mild biochemical changes associated with the disorder).

The subject may be diagnosed with, be at risk of developing or present with symptoms of a protein misfolding neurodegenerative disorder.

The subject may have, or be suspected of having (e.g. present with symptoms or a history indicative or suggestive of), a protein misfolding neurodegenerative disorder as described herein.

Accordingly, in some examples, the subject has a protein misfolding neurodegenerative disorder. In particular examples, the subject has an early stage protein misfolding neurodegenerative disorder. An example of an early stage of disease is when the subject is in the prodromal stages of a protein misfolding neurodegenerative disorder, wherein they have the initial symptoms of the disorder but have not yet developed the sufficient symptoms for diagnosis of disease.

As stated above, each of these disorders is clinically well defined and therefore at least one means for clinical diagnosis, or identifying risk factors and symptoms (including initial symptoms) associated with each disorder is well known to a person of skill in the art.

The methods described herein comprise providing, obtaining, assaying and/or analysing an extracellular vesicle sample from a subject.

The extracellular vesicle (EV) sample may be obtained from any appropriate biological sample of the subject. The methods described herein may comprise the step of obtaining the biological sample from the subject (e.g. by biopsy, removal of a blood sample, urine or saliva sampling etc). Methods for obtaining biological samples (e.g. blood samples) from a subject are well known and include, for example, established techniques used in phlebotomy.

In general, the methods described are in vitro methods that are performed using a sample that has already been obtained from the subject (i.e. the sample is provided for the method, and the steps taken to obtain the sample from the subject are not included as part of the method).

As used herein, a "biological sample" or "sample" refers to a sample obtained or derived from a subject. For the purposes described herein, the sample may be a tissue sample (e.g. a biopsy such as a brain biopsy) or it may be a fluid sample. Suitable samples include cerebrospinal fluid (CSF), blood (whole blood, or components thereof such as plasma, serum, platelets, buffy coats or combinations thereof), brain tissue homogenate, urine, saliva or a combination of any of the above. It is noted that each of these samples have been demonstrated as useful or potentially useful samples for detecting protein misfolding neurodegenerative disorders (see for example; Loov et al., 2016; Mollenhauer et al., 2011; Danzer et al., 2012; and Luk et al., 2016). Methods for obtaining each of these samples from a subject (or for isolating e.g. blood components such as plasma, platelets, serum, buffy coats etc from whole blood) are well known in the art and can routinely be used to obtain the appropriate biological sample referred to herein.

The methods described herein relate to the use of an extracellular vesicle (EV) sample obtained from a biological sample of a subject. The methods may include the step of obtaining an extracellular vesicle sample from the biological sample. Alternatively, the method may be performed on an EV sample that is provided for the method, such that the method steps themselves do not include the step of obtaining (e.g. purifying, isolating or enriching for) the extracellular vesicles from the biological sample.

The EV sample may be obtained (either as part of the method, or prior to commencing the method) by any one or more of the appropriate methods for obtaining EVs known in the art. Examples of suitable methods for obtaining an EV sample are summarised in Lobb et al., 2015; and Boing et al., 2014. As described therein, suitable methods include differential centrifugation, density-gradient ultracentrifugation, and size exclusion chromatography.

Therefore, in one example, the methods described herein comprise the steps of:
i) providing a biological sample from the subject; and
ii) obtaining an extracellular vesicle sample from the biological sample using size exclusion chromatography. The extracellular vesicle sample is then assayed for the presence of pathological prion-like protein as described elsewhere herein.

The inventors have identified that size exclusion chromatography (SEC) can advantageously be used to obtain an EV sample from a suitable biological sample, such as a brain tissue homogenate, CSF, plasma or platelet sample. Size exclusion chromatography has several advantages over differential centrifugation and density-gradient ultracentrifugation, which are the most widely applied methods for isolating EVs. As discussed in Boing et al., 2014, with SEC there is no risk of protein complex formation and vesicle aggregation. Furthermore, the high viscosity of plasma affects the recovery of vesicles isolated by differential centrifugation, but does not affect the recovery of vesicles by SEC. Compared to density-gradient ultracentrifugation, SEC is compatible with buffers with physiological osmolarity and viscosity, and the biological properties of vesicles appear unaffected after isolation by SEC. Moreover, SEC allows for isolation of contaminants with overlapping densities, such as cholesterol (which is not possible using density-gradient ultracentrifugation).

SEC separates material based on size. For example, sepharose beads in a column may be used having pores with a diameter of approximately 75 nm (reviewed in Boing et al., 2014), with a tortuous path through the beads. A particle that can enter the beads is delayed due to the increased path length. Theoretically, all particles larger than the pore diameter (e.g. larger than 75 nm in this example) cannot enter the beads and travel along with the void volume fluid only. Sepharose with this pore size (e.g. Sepharose CL-2B) has been used to confirm that this method can be used to separate EVs having a diameter of 70 nm or larger (as confirmed by EM) from smaller contaminants in the sample. Beads with smaller pores may be used to isolate vesicles of a smaller size (although likely with a concomitant increase in contamination). The bead pore size (as well as column height, column diameter and sample volume) may therefore be adjusted/optimised for the specific purpose required.

Any appropriate methodology for size exclusion chromatography can be used to obtain the EV sample described herein. Details of an appropriate methodology are provided below as non-limiting examples.

The biological sample of interest (e.g. CSF, plasma, platelets etc) may be fresh, chilled or frozen. If frozen, the biological sample may be thawed for example on ice, prior to size exclusion chromatography.

If the biological sample is a tissue sample (fresh, chilled, frozen or thawed), it may be homogenised prior to size exclusion chromatography. Details of a suitable protocol for homogenisation is provided in the examples section below.

The biological sample may be vortexed prior to size exclusion chromatography (e.g. to encourage material in the sample to go into or remain in solution).

The biological sample may be pre-cleared by centrifugation e.g. for CSF pre-clearing may comprise three sequential steps of 1500 g, 3000 g and 10,000 g, with each step being typically 10 mins in length; for plasma pre-clearing may comprise three sequential steps of 1500 g, 3000 g, and 3000 g, with each step being typically 10 min in length. After each step, the supernatant (liquid portion) is retained and used for the subsequent step.

Typical commercially available SEC columns have a maximum or optimum liquid loading volume. If the pre-cleared biological sample (i.e. the supernatant present at the end of the pre-clearing steps) has a larger volume than the maximum or optimum loading volume of the SEC column, the sample may be concentrated using any appropriate means (e.g. VivaSpin centrifugal concentrators (Sartorius)) until the optimum or maximum loading volume is obtained. For example, the inventors loaded approximately 500 µl of sample onto the SEC column—therefore in cases where more than 500 µl of pre-cleared sample was available, the inventors concentrated the sample using the VivaSpin centrifugal concentrators (Sartorius) to approximately 500 µl prior to loading onto the SEC column.

The pre-cleared (and optionally concentrated) samples may then be loaded onto an appropriate SEC column in accordance with the manufacturer's instructions. Any appropriate SEC column may be used. By way of example, for the qEV (Izon Science) standard 500 µl SEC columns used herein for CSF and plasma samples, the inventors loaded each 500 µl pre-cleared sample onto a separate column and eluted using PBS. As per the manufacturer's instructions, the first 6×500 µl fractions (collected as total 3 ml fraction) are the void volume and EVs are contained within fractions 7, 8 and 9. In this example, all three EV fractions may be collected to one tube.

The EV sample may optionally be concentrated after SEC. Any suitable methodology may be used to concentrate the EV sample. As a non-limiting example, the inventors concentrated the EV fraction (of approximately 1500 µl) to 500 µl using VivaSpin 2 (Sartorius).

The EV sample may be assayed (or analysed) immediately, or may be stored in any appropriate manner, for example it may be frozen and stored at −80° C.

As described elsewhere herein, the EV sample is obtained from a biological sample. It is a processed sample that is enriched for EVs (i.e. it has a higher concentration of EVs compared to the concentration of EVs in the biological sample from which it was generated (e.g. CSF, blood, urine, plasma etc). In this context, "enriched" or "enrichment" refers to a sample or a process in which the proportion of EVs contained within a biological sample is increased relative to other components of the sample. Enrichment may be measured by comparing the number of EVs before and after the processing of the sample, where any increase in the relative number of EVs compared to other components of the sample is considered enrichment. Enrichment and/or purity may be measured in terms of concentration compared to the biological sample (e.g. the unprocessed sample, or the pre-cleared sample) from which the EV sample has been generated, wherein the concentration of EV's is at least 10%, 15%, 20%, 25%, 30%, 35%, 40%, 45%, 50%, 55%, 60%, 65%, 70%, 75%, 80%, 85%, 90%, 95% or more higher than the concentration of EVs in the biological sample (e.g. the unprocessed sample, or the pre-cleared sample). Enrichment and/or purity may be measured in terms of the number EVs molecules such that a sample is enriched about or at least about 2×, 3×, 4×, 5×, 10×, 15×, 20×, 25×, 30×, 35×, 40×, 45×. 50×. 55×, 60×, 65×, 70×, 75×, 80×, 85×, 90×, 95×, 100×, 110×, 120×, 130×, 140×, 150×, 160×, 170×, 180×, 190×, 200×, 210×, 220×, 230×, 240×, 250×, 260×, 270×, 280×, 290×, 300×, 325×, 350×, 375×, 400×, 425×, 450×, 475×, 500×, 525×, 550×, 575×, 600×, 625×, 650×, 675×, 700×, 725×, 750×, 775×, 800×, 825×, 850×, 875×, 900×, 925×, 950×, 975×, 1000×, 1100×, 1200×, 1300×, 1400×, 1500×, 1600×, 1700×, 1800×, 1900×, 2000× (same as -fold) and all ranges derivable therein in EVs compared to the biological sample (e.g. the unprocessed sample, or the pre-cleared sample) from which the EV sample has been generated.

The level of enrichment may be determined using EM and tunable resistive pulse sensing (TRPS).

An EV sample (in other words and EV enriched sample) does not need to be 100% pure extracellular vesicles.

Preferably, the EV sample has a minimal amount of contaminating cellular or extracellular content (e.g. cellular or extracellular proteins, lipids, carbohydrates, lipoproteins etc that are not associated with EVs). In other words, the EV sample may be predominantly composed of EVs. In this context, a "minimal amount" may include less than 10% (by concentration) of contaminants, less than 5%, less than 2%, less than 1%, less than 0.5%, less than 0.25%, less than 0.1% etc (by concentration) contaminants. The level of contamination does not need to be 0%. The level of contamination may be determined using EM.

The EV sample may be an isolated sample containing substantially pure EVs. The isolated sample may be isolated from any EV-containing biological sample. The term "substantially pure" or "substantial purity" when referring to an isolated sample containing substantially pure EVs means the percentage of EVs in the population is significantly higher than that found in a biological sample (e.g. the unprocessed sample, or the pre-cleared sample) from which the EV sample has been generated (e.g., in a tissue or a blood stream of a subject). Typically, the percentage of EVs in an isolated sample containing substantially pure EVs is at least about 50%, preferably at least about 60%, 70%, 75%, and more preferably at least about 80%, 85%, 90%, 95%, 96%, 97%, 98% or 99% of the total sample.

Extracellular vesicles have been well characterised and have a well defined meaning in the art (reviewed in Andaloussi et al., 2013). Extracellular vesicles have been isolated from several bodily fluids. They have been shown to play a key role in the regulation of physiological processes, including stem cell maintenance, immune surveillance and blood coagulation. They have also been shown to play a crucial role in the pathology underlying several diseases.

In contrast to synaptic vesicles, extracellular vesicles are released intact from neurons and can either be shed from multivesicular bodies (MVBs), which are derived from endosomes, or bud directly out from the plasma membrane. When they are released into the extracellular space they are referred to as exosomes or ectosomes (or microvesicles) depending on whether they have formed from inner or outer cell membranes, and are taken up by other cells through endocytosis or fusion.

Extracellular vesicles are classified according to their cellular origin, biological function, or based on their biogenesis (reviewed in Andaloussi et al., 2013). As determined by their biogenesis, the three main classes of extracellular vesicles are exosomes, microvesicles and apoptotic bodies, the first two of which are most predominant in biological samples (and thus in EV samples derived therefrom). EV markers are well known in the art. Examples of exosome markers include tetraspanins (such as TSPAN29 and TSPAN30), ESCRT components, PDCD6IP, TSG101, flotillin, and MFGE8. Examples of microvesicle markers include integrins, selectins and CD40 ligand.

Despite recent advances, the terms "exosome" and "microvesicle" have been used interchangeably in many published studies. Herein, the term "extracellular vesicle" is used to refer to both vesicle types.

The methods described herein comprise assaying an extracellular vesicle sample from the subject for the presence of a pathological prion-like protein.

The assays used to detect a pathological prion-like protein may be of any sort known to those skilled in the art suitable for such detection. Suitably, the assays used to detect a pathological prion-like protein may detect aggregation of the prion-like protein (e.g. by measuring the rate of prion-like protein aggregation over time, or by determining the presence of or measuring the amount of aggregated prion-like protein in the sample). The assays may allow for comparison of the detected pathological prion-like protein (e.g. by measurement of the rate of prion-like protein aggregation over time, or by determination of the presence of or measurement of the amount of aggregated prion-like protein in the sample) to a reference level. The reference level may be obtained from a control sample or may be a pre-determined reference level. The control sample or pre-determined reference level may be a positive control or positive predetermined reference level (to verify that the method is working) or may be a negative control or negative predetermined reference level (such that any positive signal or detection of pathological prion-like protein over/above the negative control or negative pre-determined reference level indicates the presence of pathological prion-like protein in the subject's EV sample).

Various suitable assay types will be known to those skilled in the art, including, but not limited to: immunoEM, RT-QuIC and PMCA. Detailed methodology for each of these assays is well established in the art, as can be seen from Fairfoul et al., 2016 and Atarashi et al., 2011 (for RT-QuIC); and Herva et al., 2014, Gonzalez-Montalban et al., 2011, and Salvadore et al., 2014 (for PMCA).

In a particular example, the RT-QuIC method of Fairfoul et al., 2016 is used to assay for the presence of pathological prion-like protein in an EV sample described herein, particularly for the presence of pathological alpha-synuclein in an EV sample (such as an EV sample obtained from a biological sample selected from CSF, brain tissue homogenate, plasma, serum, platelets or buffy coats).

The assays described above (and particularly the RT-QuIC and PMCA methods described in the papers referenced above) may be adapted to determine the presence of pathological prion-like proteins other than alpha-synuclein in an EV sample of a subject, in order to identify, monitor, determine the risk of developing etc a corresponding protein misfolding neurodegenerative disorder (i.e. a protein misfolding neurodegenerative disorder that corresponds with the presence of the measured pathological prion-like protein). Examples of the different pathological prion-like proteins (and their corresponding protein misfolding neurodegenerative disorder) are described in detail above.

An in vitro method of determining the presence of a pathological prion-like protein in a subject suspected of having a protein misfolding neurodegenerative disorder or having an increased risk of developing a protein misfolding neurodegenerative disorder is therefore also provided, the method comprising:
  (a) providing an extracellular vesicle sample from the subject; and
  (b) determining the presence of a pathological prion-like protein in the extracellular vesicle sample.

The presence of a pathological prion-like protein can be determined using any of the assays described in detail above.

The extracellular vesicle sample may be provided or obtained using any of the methods described in detail above.

Appropriate subjects, terminology and permutations or combinations of features have been described in detail above.

A method of selecting a treatment for a subject having a disease is also provided, comprising determining the presence of a pathological prion-like protein in an extracellular vesicle sample from the subject, wherein the presence of a pathological prion-like protein indicates that the subject would benefit from treatment for a protein misfolding neurodegenerative disorder.

The method may be an in vitro method.

The presence of a pathological prion-like protein can be determined using any of the assays described in detail above.

The extracellular vesicle sample may be provided or obtained using any of the methods described in detail above.

Appropriate subjects, terminology and permutations or combinations of features have been described in detail above.

The method may further comprise the step of administering a treatment for a protein misfolding neurodegenerative disorder to the subject if pathological prion-like protein is present in the EV sample from the subject.

The type of treatment will vary depending on the particular pathological prion-like protein that is present (and thus the corresponding protein misfolding neurodegenerative disorder of the subject i.e. that the subject has, is suspected of having, is at risk of developing, or is suspected of being at risk of developing).

For example, if pathological alpha-synuclein protein is determined to be present, and the subject has, is suspected of having, is at risk of having, or is suspected of being at risk of having, an alpha synucleinopathy such as Parkinson's disease, dementia with Lewy bodies or multiple system atrophy, the subject may benefit from treatment with for example cholinesterase inhibitors (for DLB); levodopa (for PD). Accordingly, the method may include the step of administering cholinesterase inhibitors (for DLB); levodopa (for PD) to the subject.

As a further example, if pathological prion-like protein is determined to be present, and the subject has, is suspected of having, is at risk of having, or is suspected of being at risk of having, Creutzfeldt-Jakob disease, the subject may benefit from treatment with compounds/treatments that alleviate the symptoms presented. Accordingly, the method may include the step of administering suitable treatment compounds the subject. Suitable compounds are well known to a person of skill in the art and depend on the specific symptoms of the subject.

As a further example, if pathological amyloid beta protein is determined to be present, and the subject has, is suspected of having, is at risk of having, or is suspected of being at risk of having, Alzheimer's disease, the subject may benefit from treatment with cholinesterase inhibitors. Accordingly, the method may include the step of administering cholinesterase inhibitors to the subject.

As a further example, if pathological tau protein is determined to be present, and the subject has, is suspected of having, is at risk of having, or is suspected of being at risk of having, a tauopathy (for example Alzheimer's disease, frontotemporal Lobar degeneration, progressive supranuclear palsy or corticobasal degeneration), the subject may benefit from treatment with compounds/regimens that alleviate the symptoms presented (e.g. antidepressants or selective serotonin reuptake inhibitors (for treating behavioural symptoms), Cholinesterase inhibitors (for improving mental abilities), or Levodopa (for disease symptoms relating to movement). Accordingly, the method may include the step of administering any one or more of these suitable treatments to the subject. Other suitable treatments are well known to a person of skill in the art and depend on the specific symptoms of the subject.

As a further example, if pathological huntingtin protein is determined to be present, and the subject has, is suspected of having, is at risk of having, or is suspected of being at risk of having, Huntington's disease, the subject may benefit from treatment with compounds/regimens that alleviate the symptoms presented (for example suitable treatments include drugs to alleviate the movement disorder (e.g. tetrabenazine); antidepressants, antipsychotics and mood stabilizing drugs to alleviate psychiatric symptoms). Accordingly, the method may include the step of administering any one or more of the above mentioned suitable treatments to the subject. Other suitable treatments are well known to a person of skill in the art and depend on the specific symptoms of the subject.

As a further example, if pathological superoxide dismutase, c9orf72, or valosin protein is determined to be present, and other prion-like proteins associated with Motor Neurone disease and the subject has, is suspected of having, is at risk of having, or is suspected of being at risk of having, Motor Neurone disease, the subject may benefit from treatment with compounds/regimens that alleviate the symptoms presented (for example Riluzole and Radicava (FDA approved drugs); or other drugs to relieve symptoms e.g. antidepressants, non-steroidal anti-inflammatory drugs etc). Accordingly, the method may include the step of administering one or more of the above mentioned suitable treatments to the subject. Other suitable treatments are well known to a person of skill in the art and depend on the specific symptoms of the subject.

As a further example, if pathological atrophin protein is determined to be present, and the subject has, is suspected of having, is at risk of having, or is suspected of being at risk of having, dentatopallidorubroluysian atrophy, the subject may benefit from treatment with compounds/regimens that alleviate the symptoms presented (e.g. anti-epileptic drugs, psychotropic medications, or riluzole). Accordingly, the method may include the step of administering one or more of the above mentioned suitable treatments to the subject. Other suitable treatments are well known to a person of skill in the art and depend on the specific symptoms of the subject.

As a further example, if pathological ataxin protein (such as ataxin-1, ataxin-2 and ataxin-3) is determined to be present, and the subject has, is suspected of having, is at risk of having, or is suspected of being at risk of having, spinocerebellar ataxia, the subject may benefit from treatment with compounds/regimens that alleviate the symptoms presented (e.g. Physical therapy, or riluzole). Accordingly, the method may include the step of administering one or more of the above mentioned suitable treatments to the subject. Other suitable treatments are well known to a person of skill in the art and depend on the specific symptoms of the subject.

The use of an in vitro extracellular vesicle sample for identification or monitoring of a protein misfolding neurodegenerative disorder in a subject, or for determining the risk of developing a protein misfolding neurodegenerative disorder in a subject is also provided.

Appropriate subjects, terminology and permutations or combinations of features have been described in detail above.

An in vitro method for determining the therapeutic effect of a treatment regimen for a protein misfolding neurodegenerative disorder is also provided, the method comprising:
 a) assaying an extracellular vesicle sample from the subject for the presence of a pathological prion-like protein;
 b) repeating step a) using an extracellular vesicle sample obtained from the subject after treatment for a time interval; and
 c) comparing the level of pathological prion-like protein determined in step a) to that determined in step b), and identifying that the treatment regimen has a therapeutic effect if there is a decrease in the level of pathological prion-like protein after treatment.

Appropriate subjects, treatments, terminology and permutations or combinations of features have been described in detail above.

An in vitro method for determining a subject's compliance or adherence with a prescribed treatment regimen for a protein misfolding neurodegenerative disorder is also provided, the method comprising:
 a) assaying an extracellular vesicle sample from the subject for the presence of a pathological prion-like protein;
 b) repeating step a) using an extracellular vesicle sample obtained from the subject after the prescribed start of the treatment regimen; and
 c) comparing the level of pathological prion-like protein determined in step a) to that determined in step b), and identifying that the subject has complied or adhered with the prescribed treatment regimen if there is a decrease in the level of pathological prion-like protein after treatment.

Appropriate subjects, treatments, terminology and permutations or combinations of features have been described in detail above.

The inventors have also identified that EVs obtained from PD or DLB patient CSF samples display significant lipid changes compared to control. These data suggest that significant lipid changes in the EVs of patients are crucial in disease state. Without being bound to a particular theory, it is thought that these lipid changes constitute part of the high sensitivity and specificity of the methods for detecting pathological alpha synuclein described herein as the alpha synuclein aggregation assay may be responsive to both alterations—ceramides and synuclein folding. The changes in ceramides in the disease state are very significant and similar to changes that are observed in the patient's brain tissue (for both PD and DLB patients; data unpublished). Advantageously, the changes in lipid composition can be used as a biomarker for detecting, monitoring and identifying disease (or risk of disease), particularly in respect of alpha synucleinopathies, more particularly in respect of PD and/or DLB.

An in vitro method of identifying or monitoring an alpha synucleinopathy in a subject is therefore provided, the method comprising:
 a) assessing the amount of at least one ceramide species selected from the group consisting of Cer 32:1, Cer 33:1, Cer 34:1, Cer 34:2, Cer 37:1, Cer 38:1, Cer 38:2, Cer 39:1, Cer 39:2, Cer 40:1, Cer 40:2, Cer 41:1, Cer 41:2, Cer 40:1(OH) and Cer 40:2(OH) in an extracellular vesicle sample of the subject; and
 b) comparing the assessed amount of the at least one ceramide species with a reference value for the at least one ceramide species;

wherein an assessed amount of the at least one ceramide species greater than the reference value for the at least one ceramide species is indicative of an alpha synucleinopathy.

An in vitro method of determining the risk of a subject developing an alpha synucleinopathy is also provided, comprising:
a) assessing the amount of at least one ceramide species selected from the group consisting of Cer 32:1, Cer 33:1, Cer 34:1, Cer 34:2, Cer37:1, Cer 38:1, Cer 38:2, Cer 39:1, Cer 39:2, Cer 40:1, Cer 40:2, Cer 41:1, Cer 41:2, Cer 40:1(OH) and Cer 40:2(OH) in an extracellular vesicle sample of the subject; and
b) comparing the assessed amount of the at least one ceramide species with a reference value for the at least one ceramide species;
wherein an assessed amount of the at least one ceramide species greater than the reference value for the at least one ceramide species is indicative of an increased risk of the subject developing an alpha synucleinopathy.

As described elsewhere herein, the alpha synucleinopathy may be selected from the group consisting of Parkinson's disease (including Parkinson's disease dementia), dementia with Lewy bodies and Multiple System Atrophy. In particular, the alpha synucleinopathy may be Parkinson's disease or dementia with Lewy bodies.

As described elsewhere herein, the method may further comprise the steps of:
i) providing a biological sample from the subject; and
ii) obtaining an extracellular vesicle sample from the biological sample using size exclusion chromatography.

Suitable subjects, extracellular vesicle samples, biological samples, methods for obtaining extracellular vesicle samples, terminology and combinations or permutations of features are described elsewhere herein and apply equally to the ceramide aspects described herein.

Suitable methods for assessing the amount of at least one of the ceramide species recited above are well known in the art. Non-limiting examples include the methods used in the examples section below; i.e. liquid chromatography-mass spectrometry (LC-MS), for example using a high resolution Thermo Orbitrap Exactive system in positive and negative ion modes (e.g. using C18 and HILIC columns). Other appropriate methods are well known to a person of skill in the art.

The assessed amount of the at least one ceramide species is compared with a reference value for the same ceramide species. For example, if the amount of Cer 32:1 and Cer 33:1 are assessed in step a) of the method, step b) of the method comprises comparing the amount of Cer 32:1 from step a) to a reference value for Cer 32:1; and comparing the amount of Cer 33:1 from step a) to a reference value for Cer 33:1 etc.

The method is indicative of an alpha synucleinopathy in the subject when, during the comparison step (step b)) the assessed amount in step a) is greater than the corresponding reference value.

The method may assess the amount of at least one, at least two, at least three, at least four, at least five, at least six, at least seven, at least eight, at least nine, at least ten, at least eleven, at least twelve, at least thirteen, at least fourteen or all fifteen of the ceramide species recited above.

More than one ceramide species may be assessed within the method. In this example if the amount of at least one (and optionally all) of the tested ceramide species is greater than the reference value these ceramide species, it is indicative of an alpha synucleinopathy (or an increased risk of the subject developing an alpha synucleinopathy). By way of example, if the amount of at least one, at least two, at least three, at least four, at least five, at least six, at least seven, at least eight, at least nine, at least ten, at least eleven, at least twelve, at least thirteen, at least fourteen or all fifteen of the ceramide species recited above is greater than the reference value these ceramide species, it is indicative of an alpha synucleinopathy (or an increased risk of the subject developing an alpha synucleinopathy).

The reference value may be obtained from a control sample or may be a pre-determined reference value.

As used herein or "control sample", refers to a sample having no pathological prion-like protein, for example a sample from a healthy subject not having or suspected or having a protein misfolding neurodegenerative disorder or alternatively a sample from the same subject that the biological test sample is obtained from, for example a sample obtained prior to any clinical symptoms or risk factors for developing a protein misfolding neurodegenerative disorder. Other appropriate control samples can easily be identified by a person of skill in the art.

As used herein, a "predetermined reference value" refers to a reference level that may be comprised from a reference database, which may be used to generate a pre-determined cut off value, i.e. a diagnostic score that is statistically predictive of a symptom or disease or lack thereof or may be a pre-determined reference level based on a standard population sample, or alternatively, a pre-determined reference level based on a subject's base line level of expression, i.e. prior to prior to any clinical symptoms or risk factors for developing a protein misfolding neurodegenerative disorder. Appropriate predetermined reference values can easily be identified by a person of skill in the art.

Suitable subjects, extracellular vesicle samples, biological samples, methods for obtaining extracellular vesicle samples, methods for assessing the amount of ceramide species, combinations of ceramide species for analysis, reference levels, terminology and combinations or permutations of features are described elsewhere herein and apply equally to this aspect.

An in vitro method of assessing the amount of at least one ceramide species selected from the group consisting of Cer 32:1, Cer 33:1, Cer 34:1, Cer 34:2, Cer37:1, Cer 38:1, Cer 38:2, Cer 39:1, Cer 39:2, Cer 40:1, Cer 40:2, Cer 41:1, Cer 41:2, Cer 40:1(OH) and Cer 40:2(OH) in a subject suspected of having an alpha synucleinopathy or having an increased risk of developing an alpha synucleinopathy is also provided, the method comprising:
(a) providing an extracellular vesicle sample from the subject; and
(b) assessing the amount of at least one ceramide species selected from the group consisting of Cer 32:1, Cer 33:1, Cer 34:1, Cer 34:2, Cer37:1, Cer 38:1, Cer 38:2, Cer 39:1, Cer 39:2, Cer 40:1, Cer 40:2, Cer 41:1, Cer 41:2, Cer 40:1(OH) and Cer 40:2(OH) in the extracellular vesicle sample.

The amount of the at least one ceramide species can be determined using any of the assays described in detail above.

The extracellular vesicle sample may be provided or obtained using any of the methods described in detail above.

Appropriate subjects, terminology and permutations or combinations of features have been described in detail above.

A method of selecting a treatment for a subject having a disease is also provided, the method comprising:
a) assessing the amount of at least one ceramide species selected from the group consisting of Cer 32:1, Cer 33:1, Cer 34:1, Cer 34:2, Cer37:1, Cer 38:1, Cer 38:2, Cer 39:1, Cer 39:2, Cer 40:1, Cer 40:2, Cer 41:1, Cer 41:2, Cer 40:1(OH) and Cer 40:2(OH) in an extracellular vesicle sample of the subject; and b) comparing the assessed amount of the at least one ceramide species with a reference value for the at least one ceramide species;

wherein an assessed amount of the at least one ceramide species greater than the reference value for the at least one ceramide species indicates that the subject would benefit from treatment for an alpha synucleinopathy.

The method may be an in vitro method.

The amount of the at least one ceramide species can be determined using any of the assays described in detail above.

The extracellular vesicle sample may be provided or obtained using any of the methods described in detail above.

Appropriate subjects, terminology and permutations or combinations of features have been described in detail above.

The method may further comprise the step of administering a treatment for an alpha synucleinopathy to the subject if the amount of the at least one ceramide species in the EV sample from the subject is greater than the reference value for the at least one ceramide species.

For example, if pathological alpha-synuclein protein is determined to be present, and the subject has, is suspected of having, is at risk of having, or is suspected of being at risk of having, an alpha synucleinopathy such as Parkinson's disease, dementia with Lewy bodies and multiple system atrophy, the subject may benefit from treatment with cholinesterase inhibitors (for DLB) or levodopa (for PD). Accordingly, the method may include the step of administering cholinesterase inhibitors (for DLB) or levodopa (for PD) to the subject.

Suitable subjects, extracellular vesicle samples, biological samples, methods for obtaining extracellular vesicle samples, terminology and combinations or permutations of features are described elsewhere herein and apply equally to the ceramide aspects described herein.

Use of at least one extracellular vesicle ceramide species selected from the group consisting of Cer 32:1, Cer 33:1, Cer 34:1, Cer 34:2, Cer37:1, Cer 38:1, Cer 38:2, Cer 39:1, Cer 39:2, Cer 40:1, Cer 40:2, Cer 41:1, Cer 41:2, Cer 40:1(OH) and Cer 40:2(OH) for identification or monitoring of an alpha synucleinopathy in a subject, or for determining the risk of developing an alpha synucleinopathy in a subject is also provided.

Appropriate subjects, terminology and permutations or combinations of features have been described in detail above.

An in vitro method for determining the therapeutic effect of a treatment regimen for an alpha synucleinopathy is also provided, the method comprising:

a) assessing the amount of at least one ceramide species selected from the group consisting of Cer 32:1, Cer 33:1, Cer 34:1, Cer 34:2, Cer37:1, Cer 38:1, Cer 38:2, Cer 39:1, Cer 39:2, Cer 40:1, Cer 40:2, Cer 41:1, Cer 41:2, Cer 40:1(OH) and Cer 40:2(OH) in an extracellular vesicle sample of the subject; and b) repeating step a) using an extracellular vesicle sample obtained from the subject after treatment for a time interval; and c) comparing the amount of the at least one ceramide species determined in step a) to that determined in step b), and identifying that the treatment regimen has a therapeutic effect if there is a decrease in the amount of the at least one ceramide species after treatment.

Appropriate subjects, treatments, terminology and permutations or combinations of features have been described in detail above.

An in vitro method for determining a subject's compliance or adherence with a prescribed treatment regimen for an alpha synucleinopathy is also provided, the method comprising:

a) assessing the amount of at least one ceramide species selected from the group consisting of Cer 32:1, Cer 33:1, Cer 34:1, Cer 34:2, Cer37:1, Cer 38:1, Cer 38:2, Cer 39:1, Cer 39:2, Cer 40:1, Cer 40:2, Cer 41:1, Cer 41:2, Cer 40:1(OH) and Cer 40:2(OH) in an extracellular vesicle sample of the subject; and b) repeating step a) using an extracellular vesicle sample obtained from the subject after the prescribed start of the treatment regimen; and c) comparing the amount of the at least one ceramide species determined in step a) to that determined in step b), and identifying that the subject has complied or adhered with the prescribed treatment regimen if there is a decrease in the amount of the at least one ceramide species after treatment.

Appropriate subjects, treatments, terminology and permutations or combinations of features have been described in detail above.

EXAMPLES

The data presented herein show that by combining the use of extracellular vesicles and the RTQUIC method, the sensitivity of the method in detecting the pathological protein aggregation is increased.

The inventors have tested extracellular vesicles purified from post-mortem cerebrospinal fluid, plasma and platelets using a routine RTQUIC assay and the sensitivity of the assay in detecting alpha-synuclein pathology is significantly increased compared to the use of raw (not purified) specimen.

Initial Analyses 15 samples of post-mortem cerebrospinal fluid (11 Parkinson's disease+dementia with Lewy bodies (synucleinopathies) and 4 controls). All cases clinically and neuropathologically validated.

Figure 2:
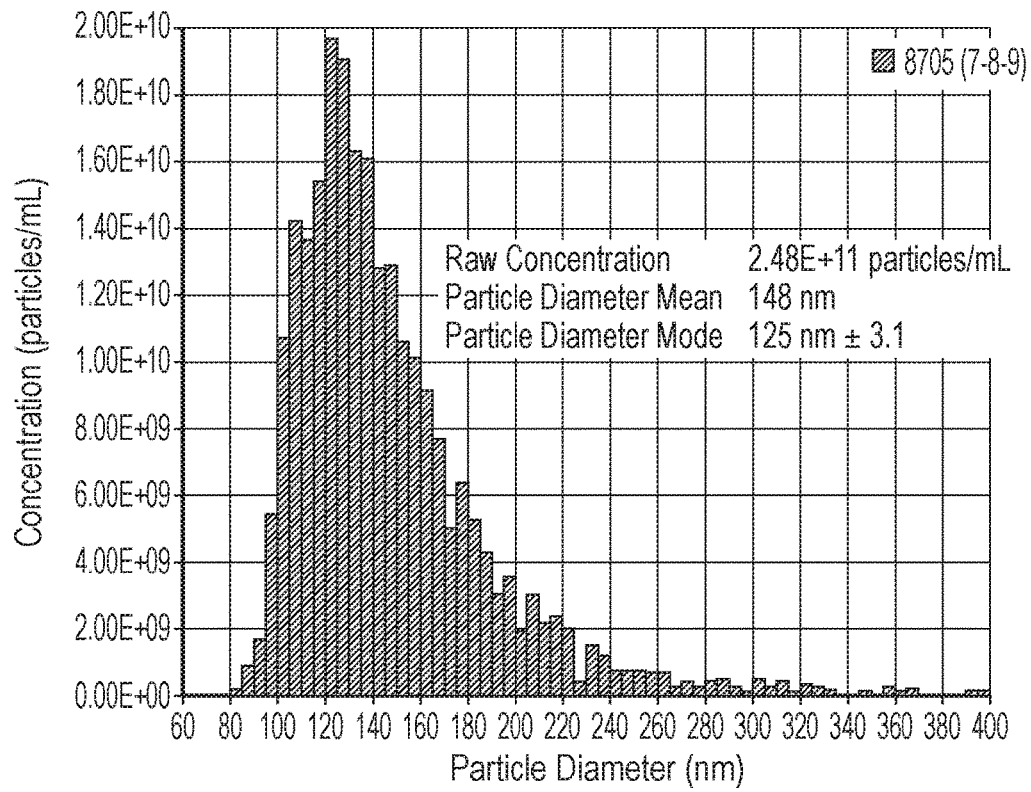
FIG. 2 shows a representative image of TRPS analysis results showing the size and concentration of vesicles.
Figure 3:
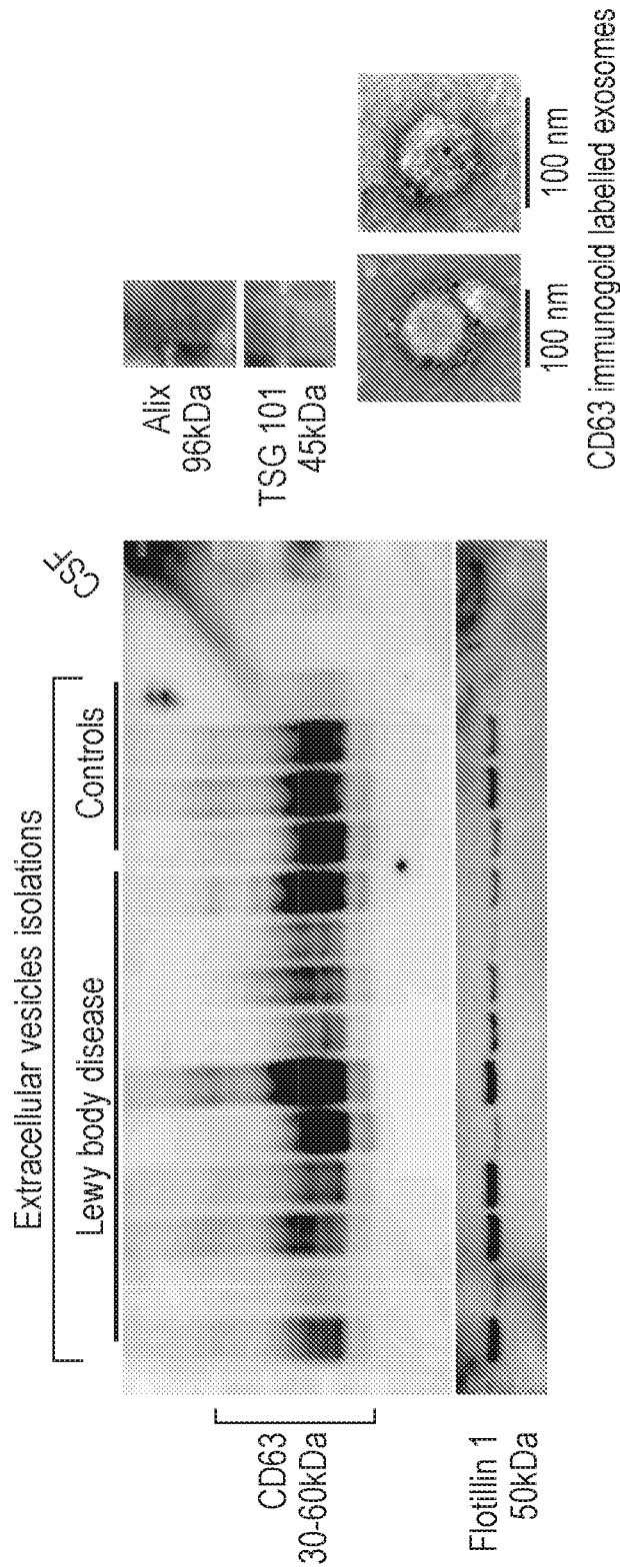
FIG. 3 shows representative images of Western blot analysis and immuno-electron microscopy of exosome marker presence in the samples.

Extracellular vesicles were purified from all cases using size exclusion chromatography. Vesicles were then analysed by tunable resistive pulse sensing (TRPS) for their size and concentration (FIGS. 1 and 2), and Western blot and immuno-electron microscopy for the presence of accepted markers (FIG. 3).

Figure 4:
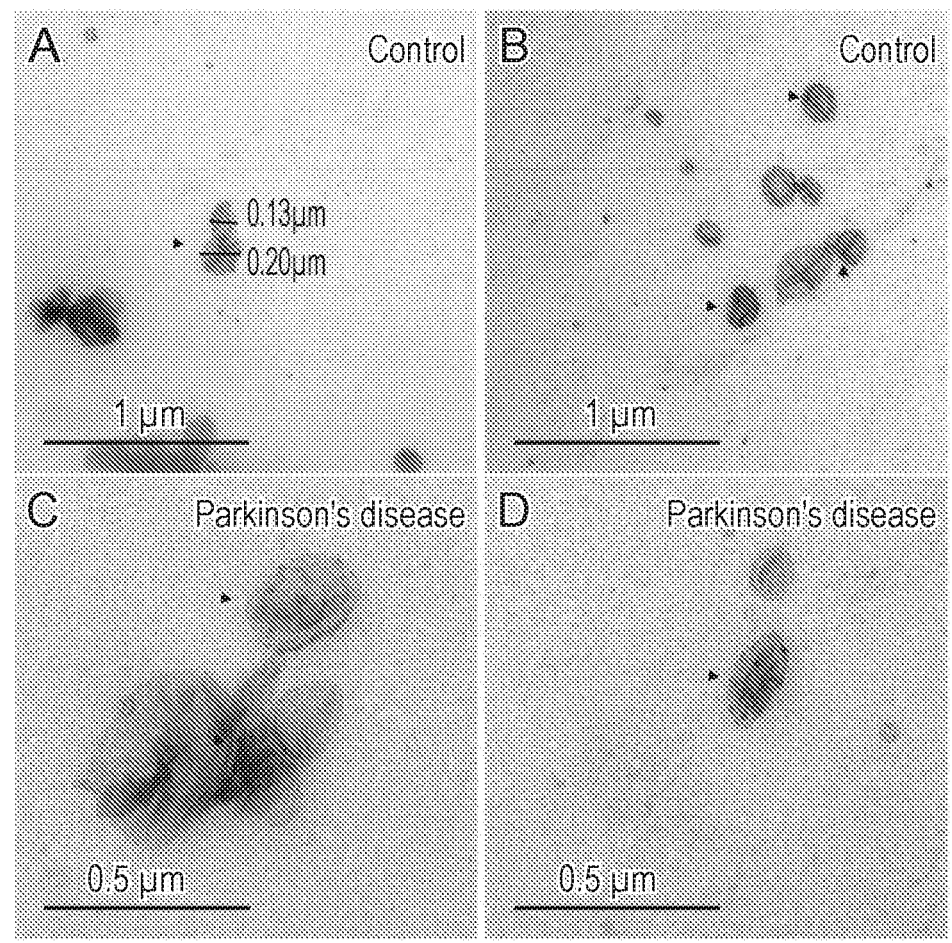
FIG. 4 shows immunogold labelling of alpha-synuclein associated with membranes of extracellular vesicles purified from post-mortem cerebrospinal fluid. Graph represents the abundance of various vesicle sizes labelled by alpha-synuclein. The data was pooled across all samples, so represents a mixed population.
Figure 4:
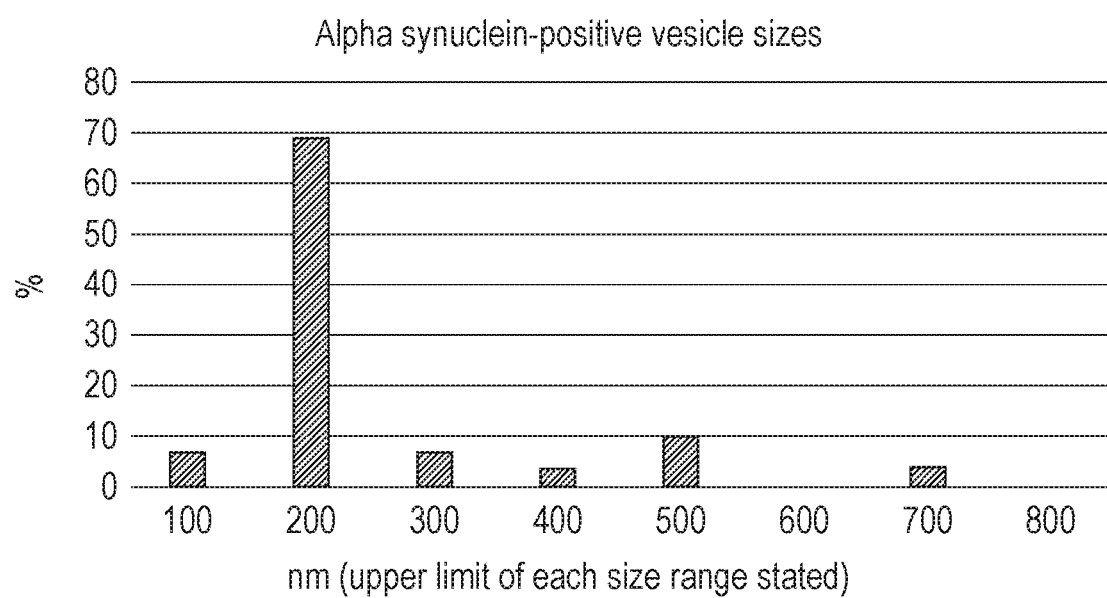
Figure 5:
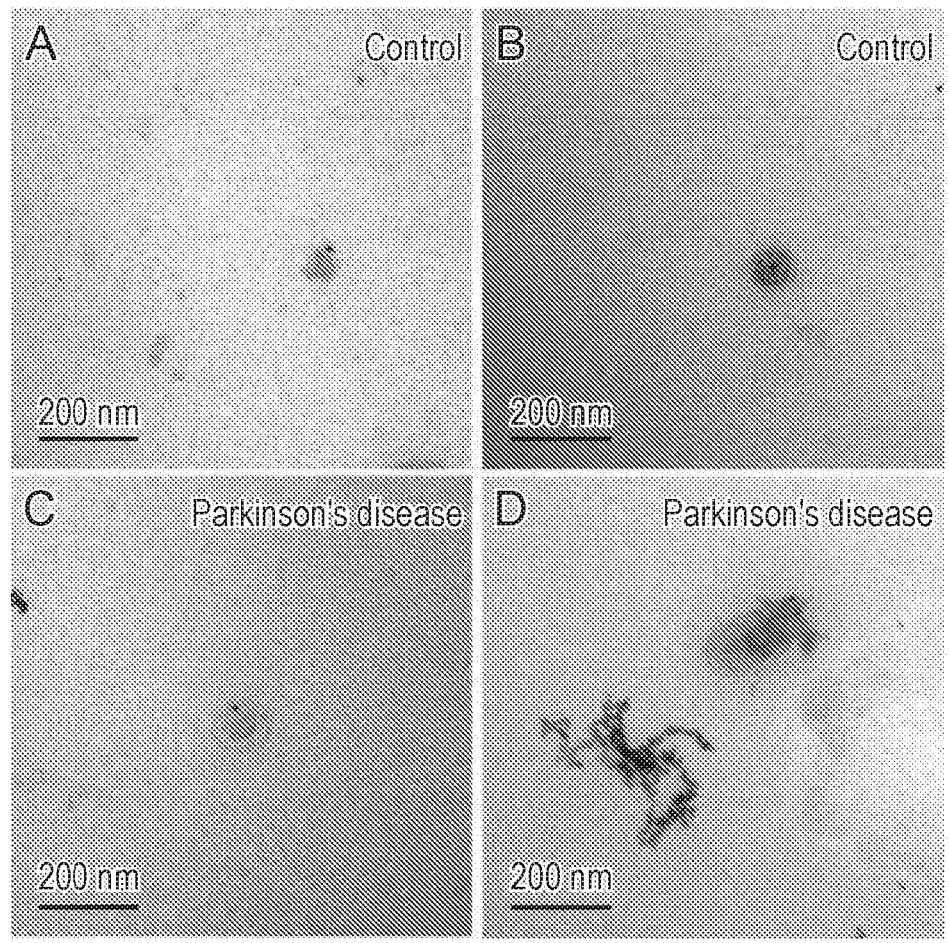
FIG. 5 shows internal alpha-synuclein labelling and various vesicle sizes labelled by alpha-synuclein. The data was pooled across all samples, so represents a mixed population
Figure 5:
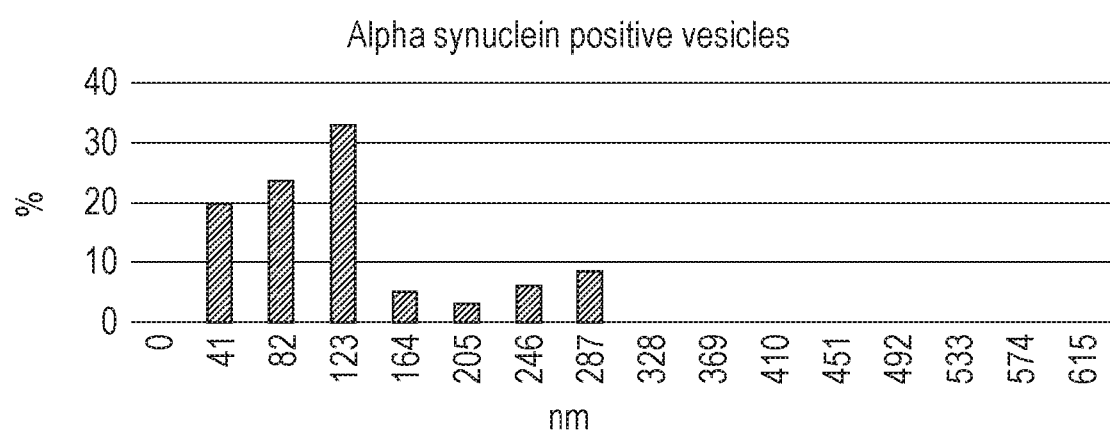

The inventors then screened all samples for the presence of alpha-synuclein using immuno-electron microscopy. They detected alpha-synuclein associated with the vesicles membranes and internal alpha-synuclein. Synuclein presence was detected in patient and control samples. One PD sample did not show any alpha-synuclein labelling at all. Alpha-synuclein seemed to be associated with membranes of larger vesicles (mean diameter 221 nm), whereas the internal alpha-synuclein labelling was characteristic for smaller vesicles (mean diameter 122 nm) (FIGS. 4 and 5). This observation was characteristic for patient and control vesicles.

Figure 6:
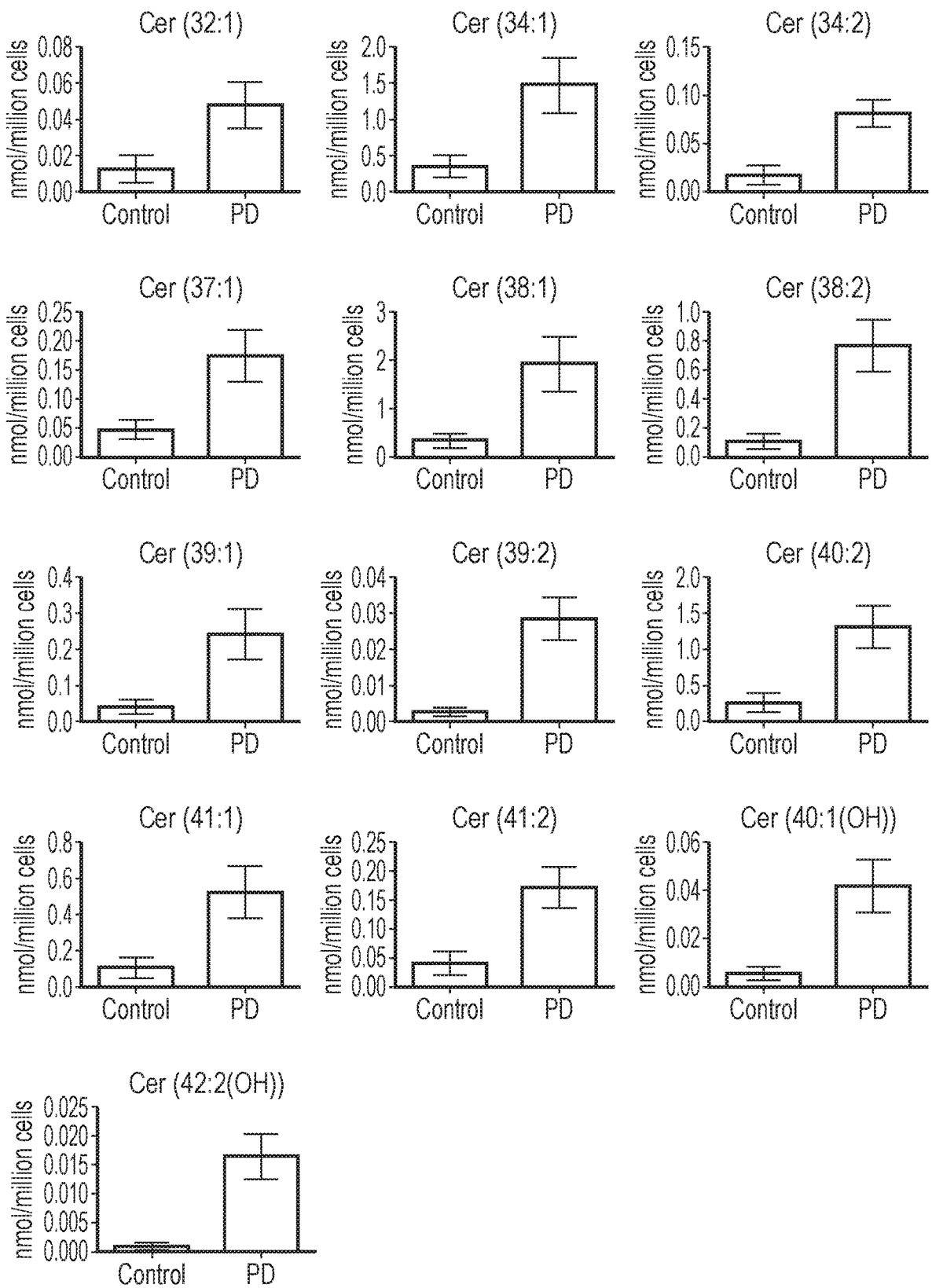
FIG. 6 shows changes in ceramide species identified in EVs from alpha synucleinopathy patients compared to controls. Positive ion mode data.
Figure 7:
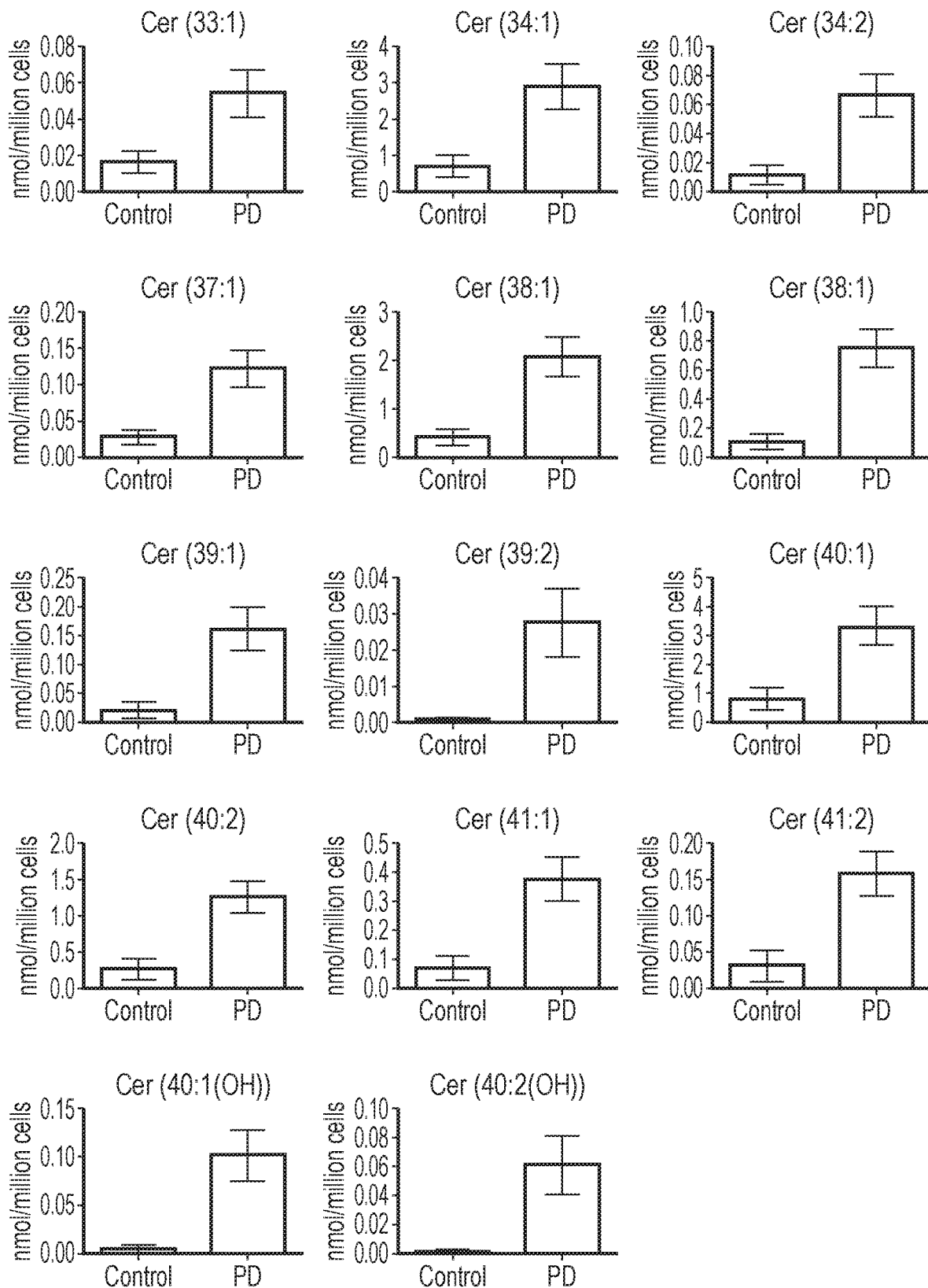
FIG. 7 shows changes in ceramide species identified in EVs from alpha synucleinopathy patients compared to controls. Negative ion mode data.

The inventors have performed global lipidomic analysis of all vesicles using liquid chromatography-mass spectrometry (LC-MS) in positive and negative ion modes employing the C18 and HILIC columns. They have identified significant changes in the abundance of ceramide species in vesicles from PD and DLB patients compared to control vesicles (FIGS. 6 and 7).

Without being bound to any particular theory, one explanation of these data is that it is not simply alpha-synuclein that is changed in the EVs but rather that the EV composition itself is changed and that the change in composition alters how the RTQUIC assay responds and/or alpha-synuclein within the EVs.

Work on Extracellular Vesicles Purified from the Frontal Cortex Brain Tissue.

Figure 8:
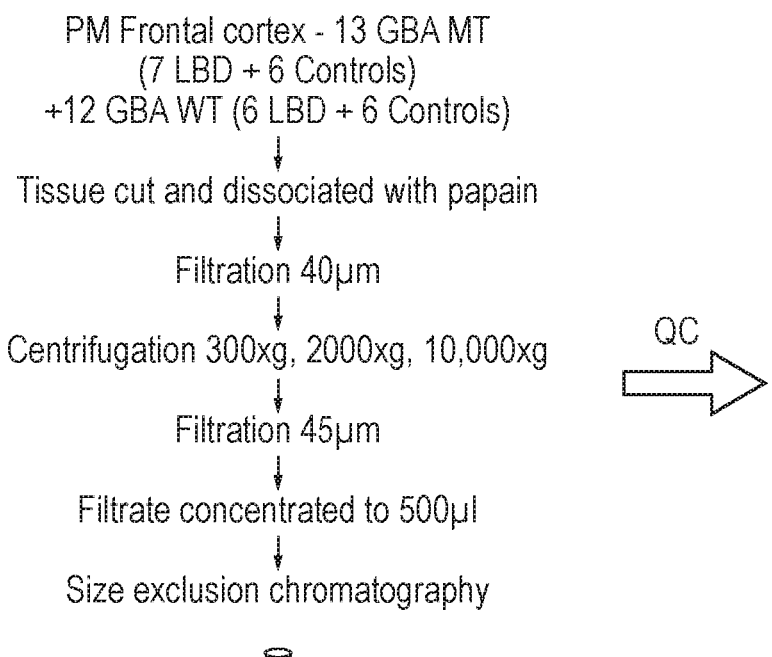
FIG. 8 shows frontal cortex extracellular vesicles purification and analysis.
Figure 8:
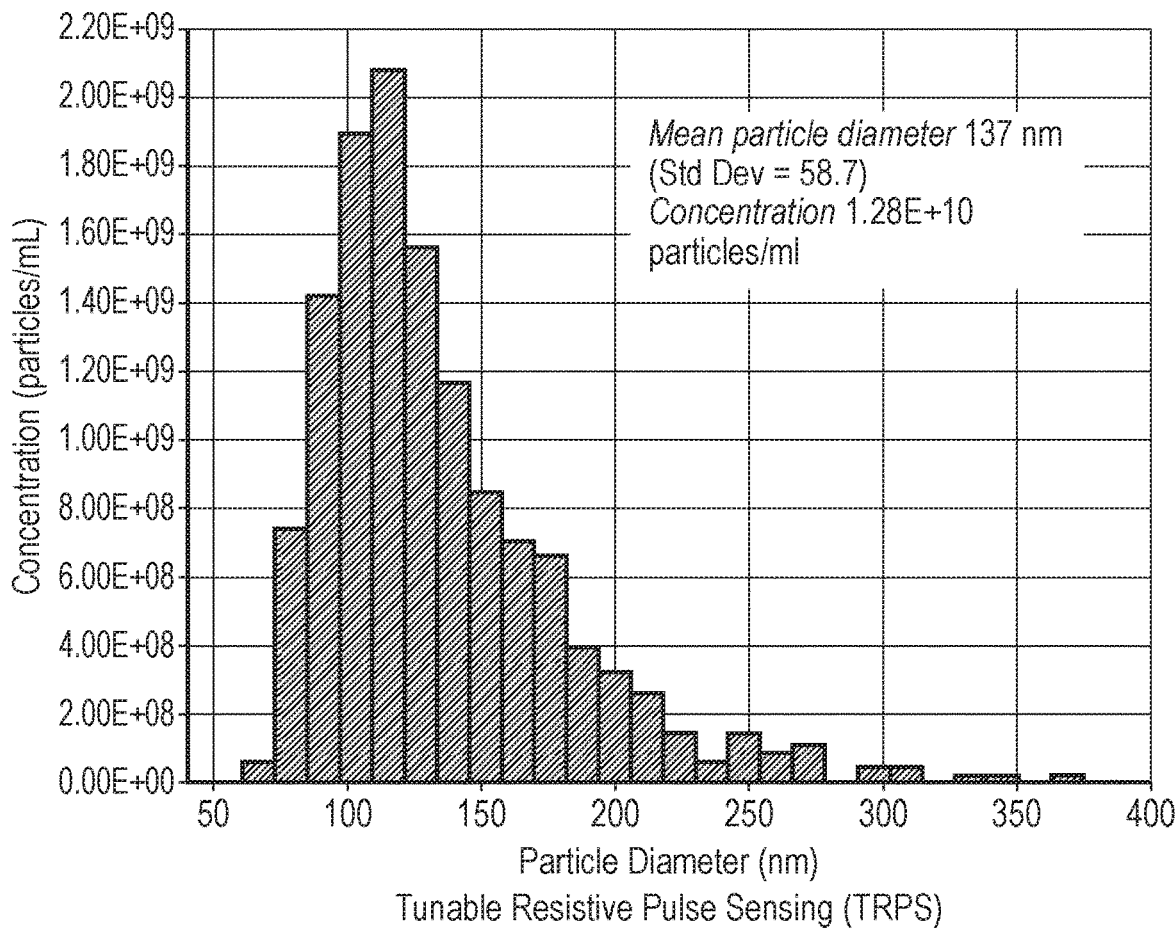
Figure 8:
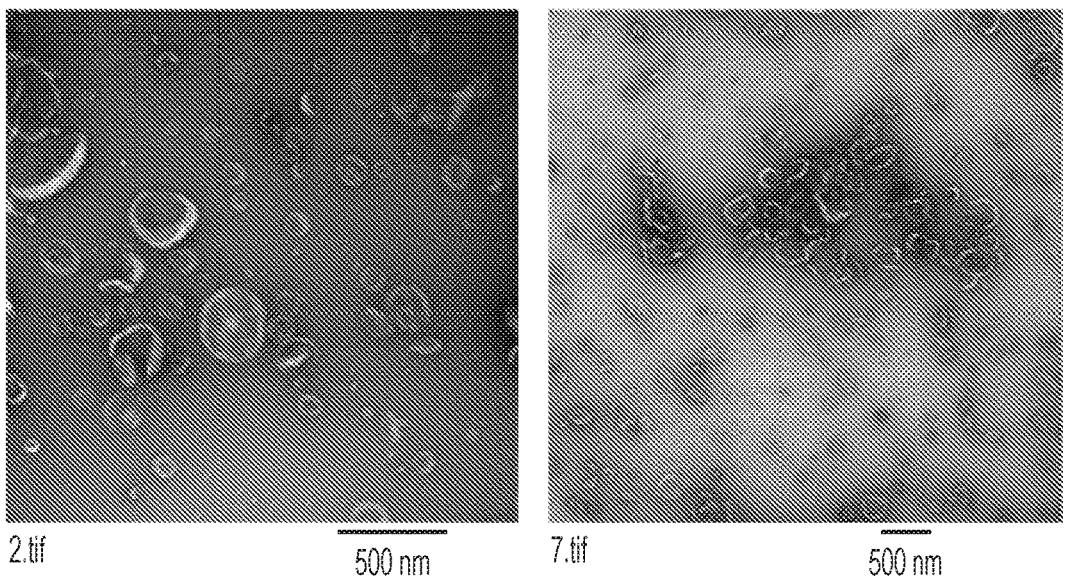
Figure 9:
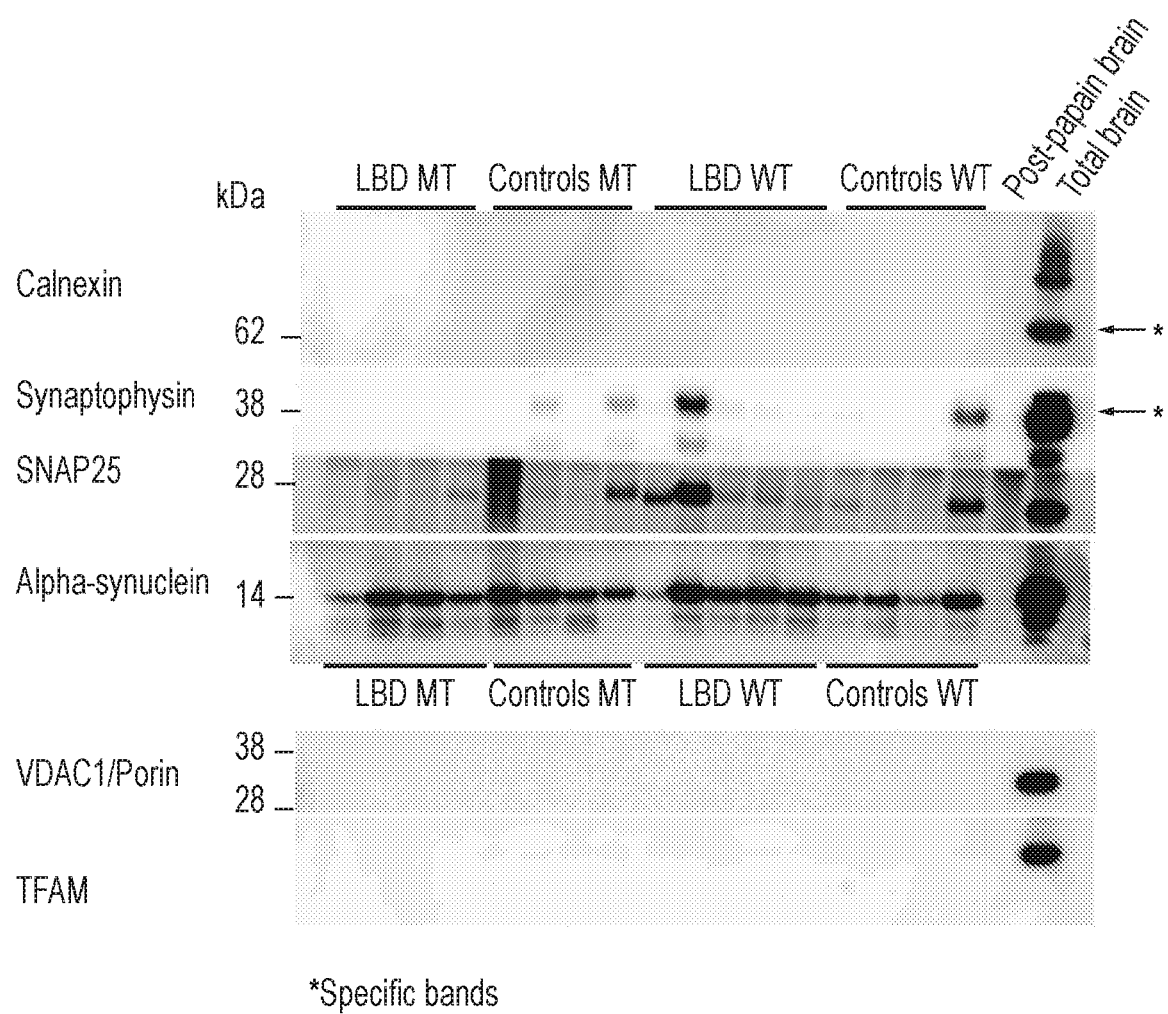
FIG. 9 shows Western blot analysis of purified frontal cortex extracellular vesicles markers. Absence of calnexin and porin indicates purity of fractions and lack of contamination with cellular and synaptic material. LBD—Lewy body disease. MT, WT—mutant, wild type.
Figure 10:
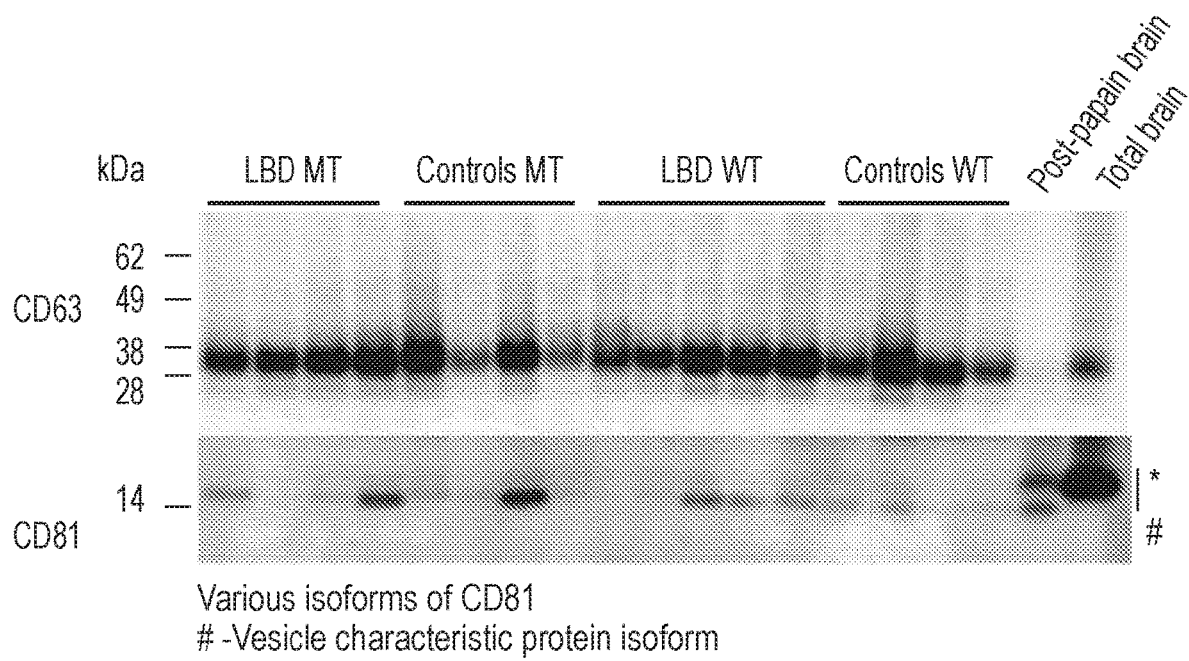
FIG. 10 shows Western blot analysis of exosomal markers.
Figure 11:
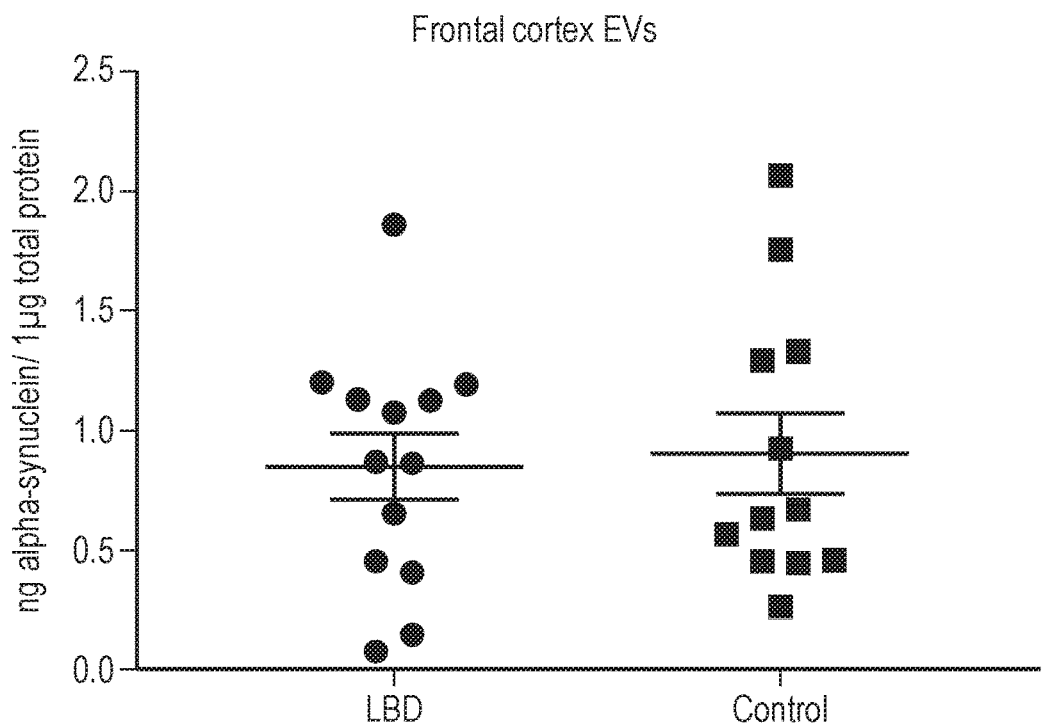
FIG. 11 shows the results of an alpha-synuclein ELISA on lysed frontal cortex vesicles.
Figure 12:
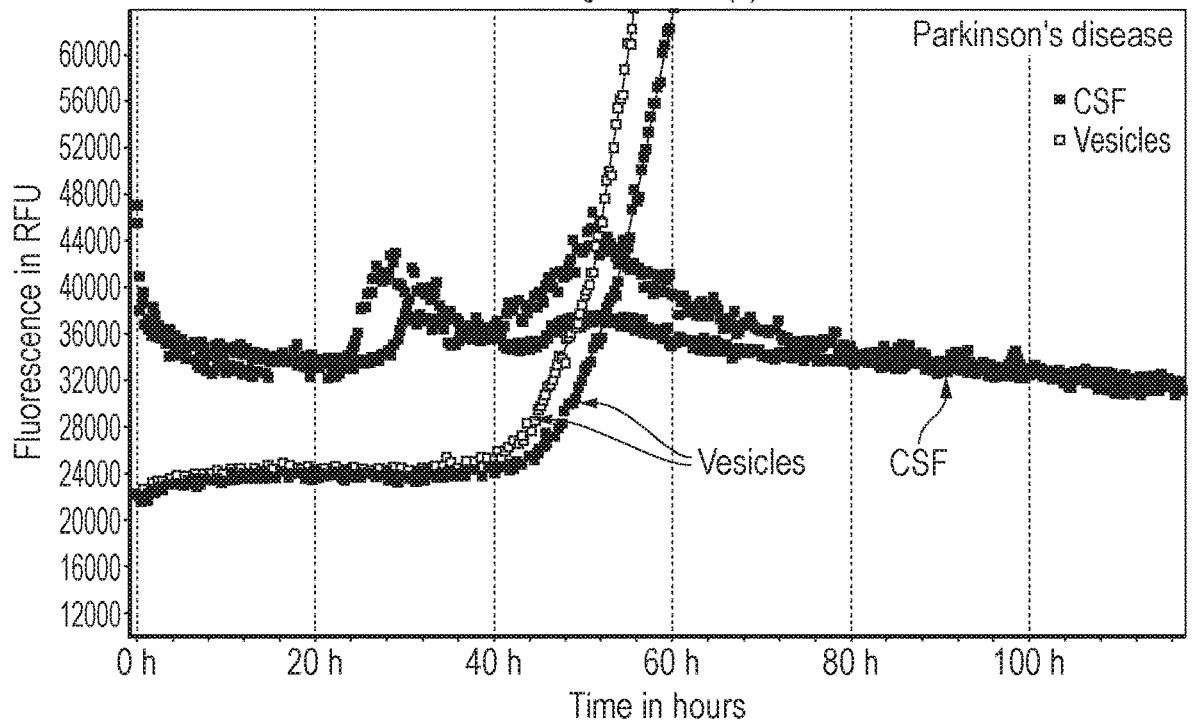
FIG. 12 shows RT-QUIC results using unprocessed post-mortem CSF and purified extracellular vesicles. By using post-mortem CSF derived vesicles the inventors were able to detect Parkinson's disease pathology (exponential lines indicate robust detection of disease features), even before the clinical symptoms occur (see prodromal synucleinopathy). PD-Parkinson's disease, DLB—dementia with Lewy bodies, PDD—Parkinson's disease dementia. The assay's positive signal could be detected earlier in comparison to the original method using unprocessed lumbar CSF (presented in Fairfoul et al. 2016), which has the potential to make the assay faster i.e. 48-80 hours (with no additional optimisation) compared to 120 hours (current length of the assay).
Figure 12:
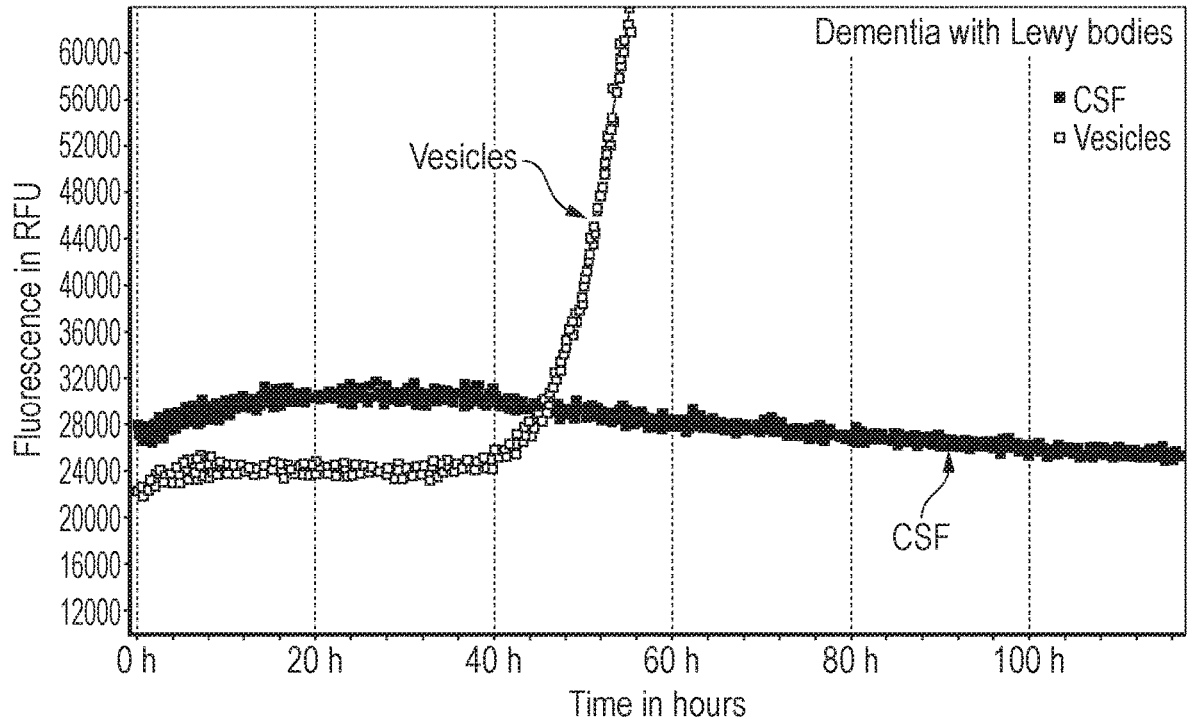
Figure 12:
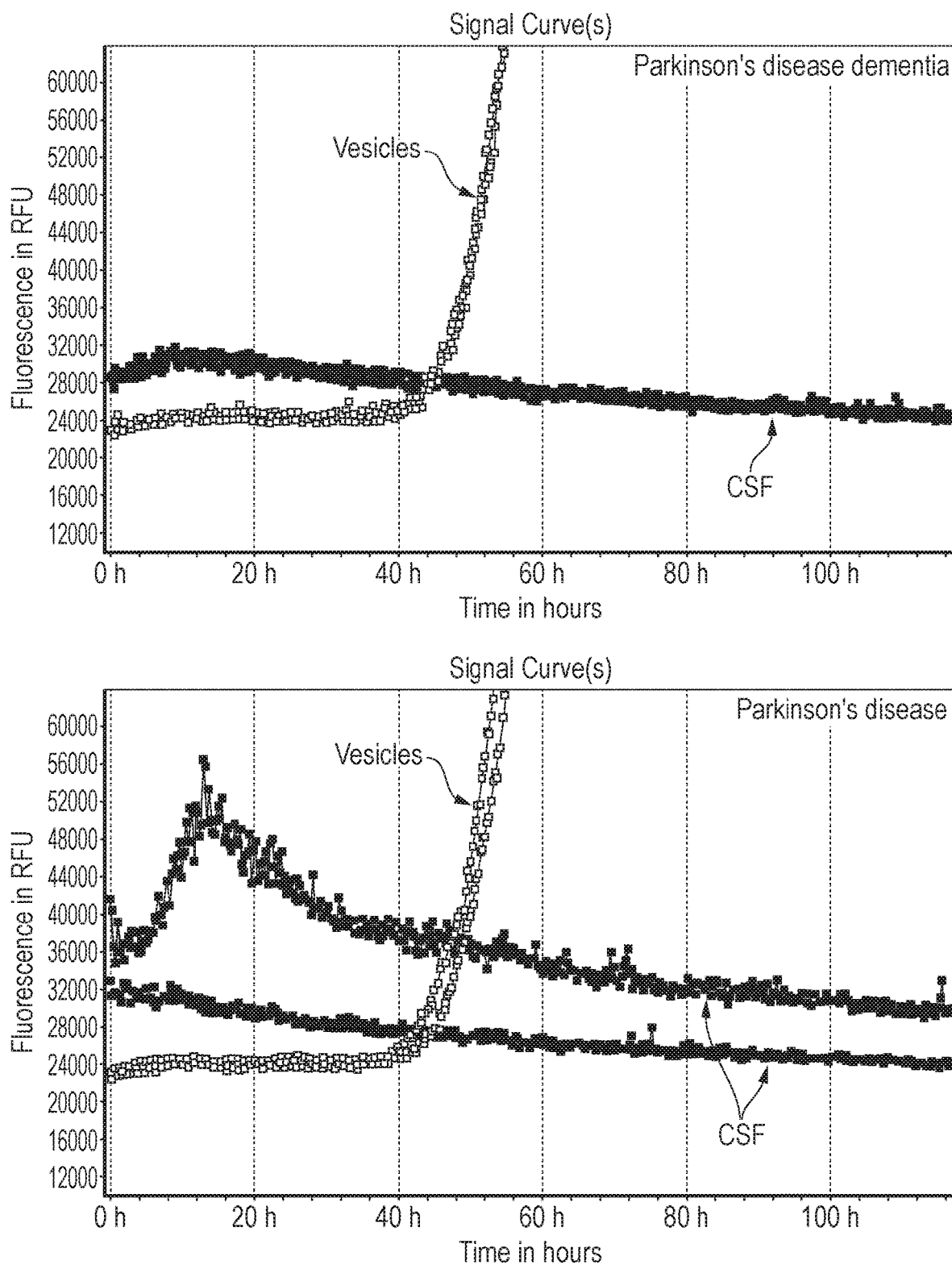
Figure 12:
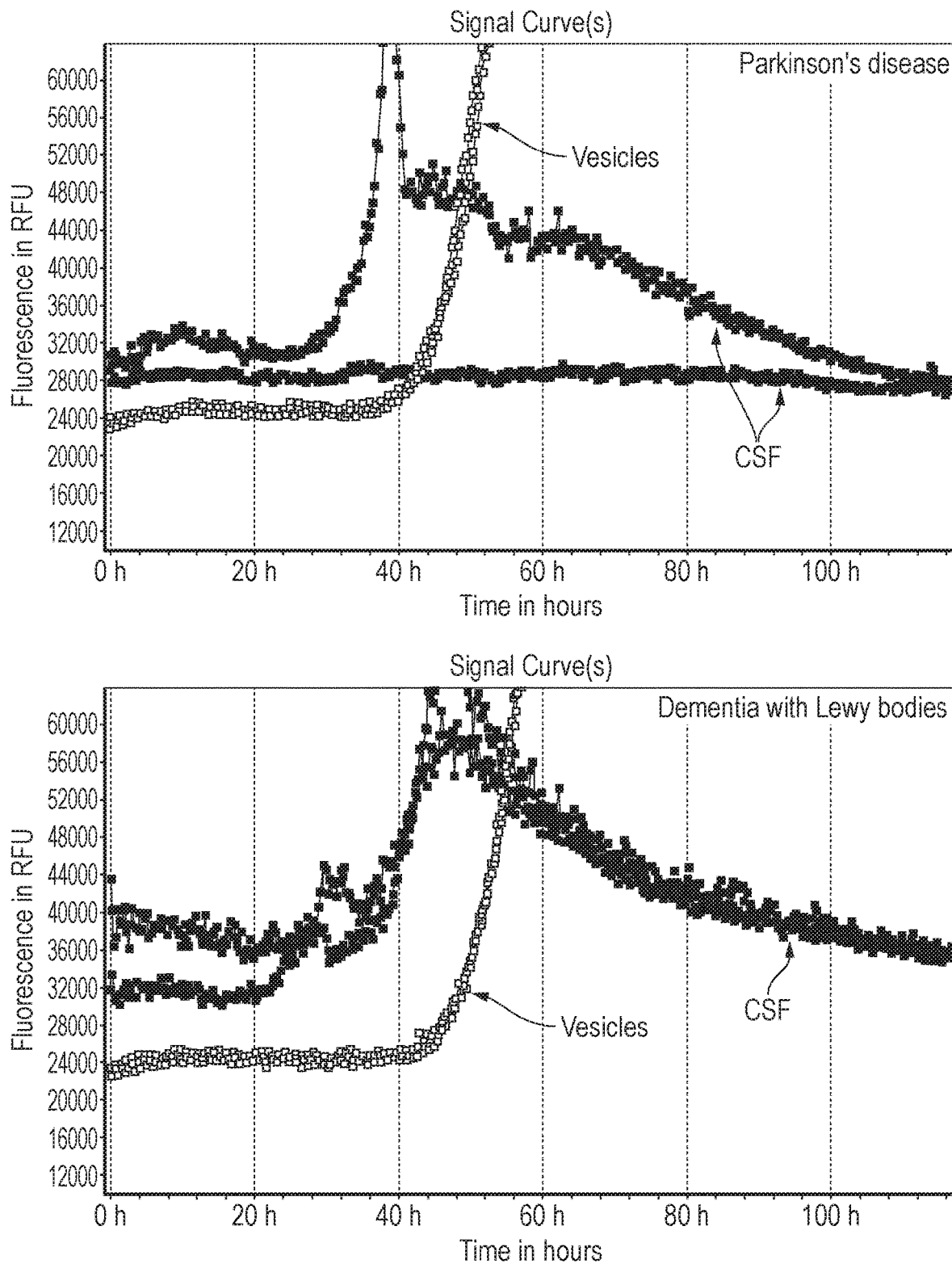
Figure 12:
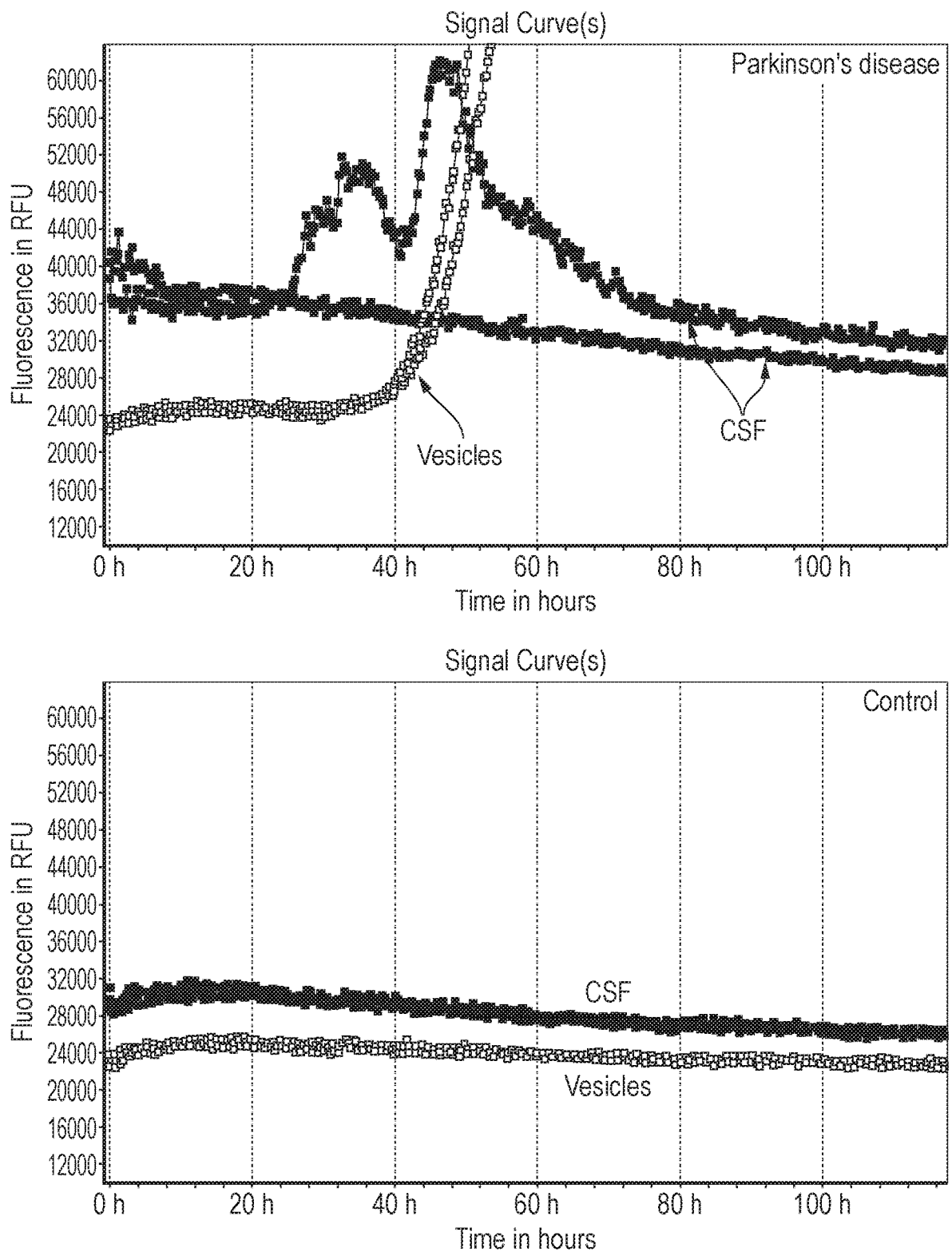
Figure 12:
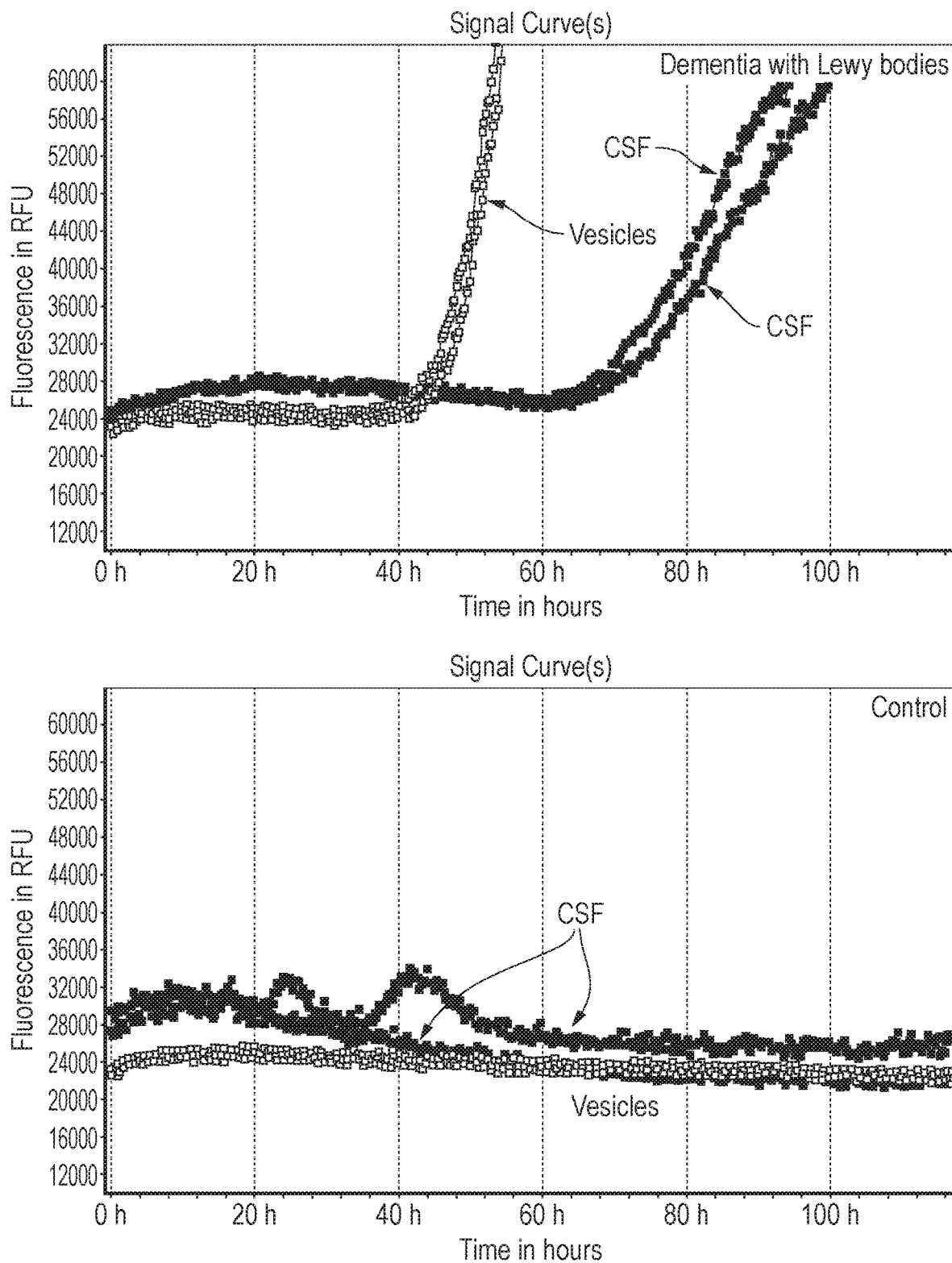
Figure 12:
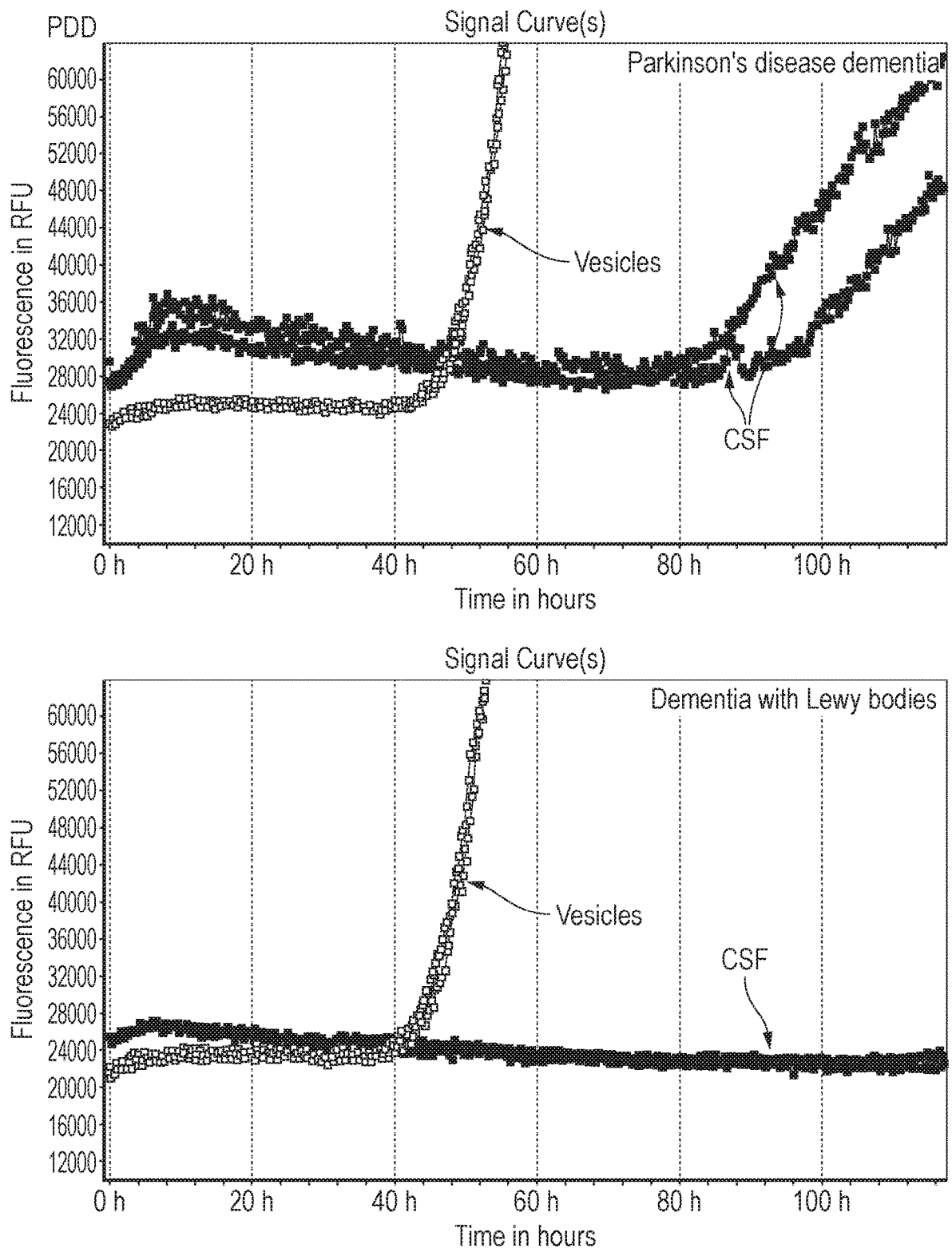
Figure 12:
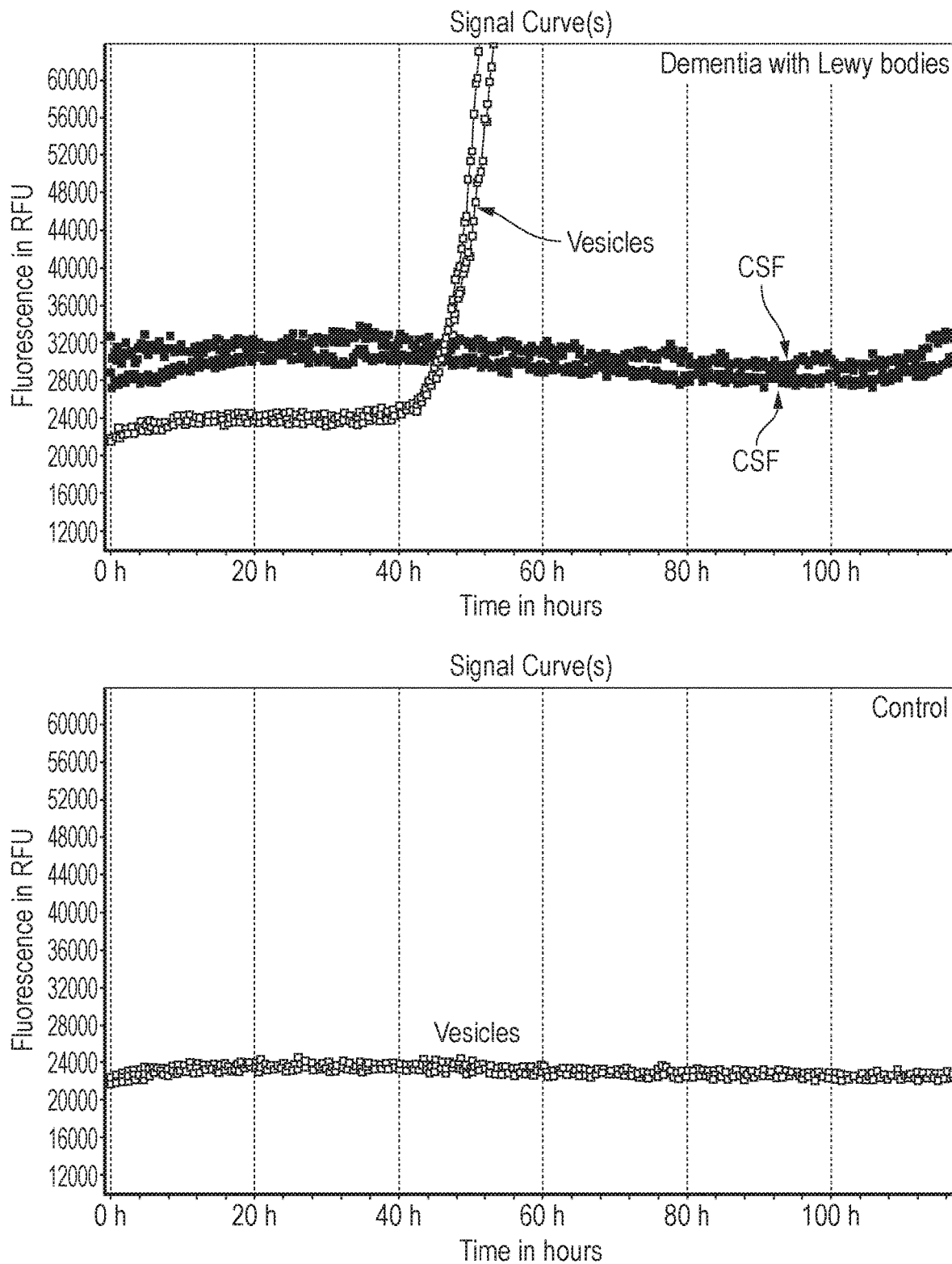
Figure 12:
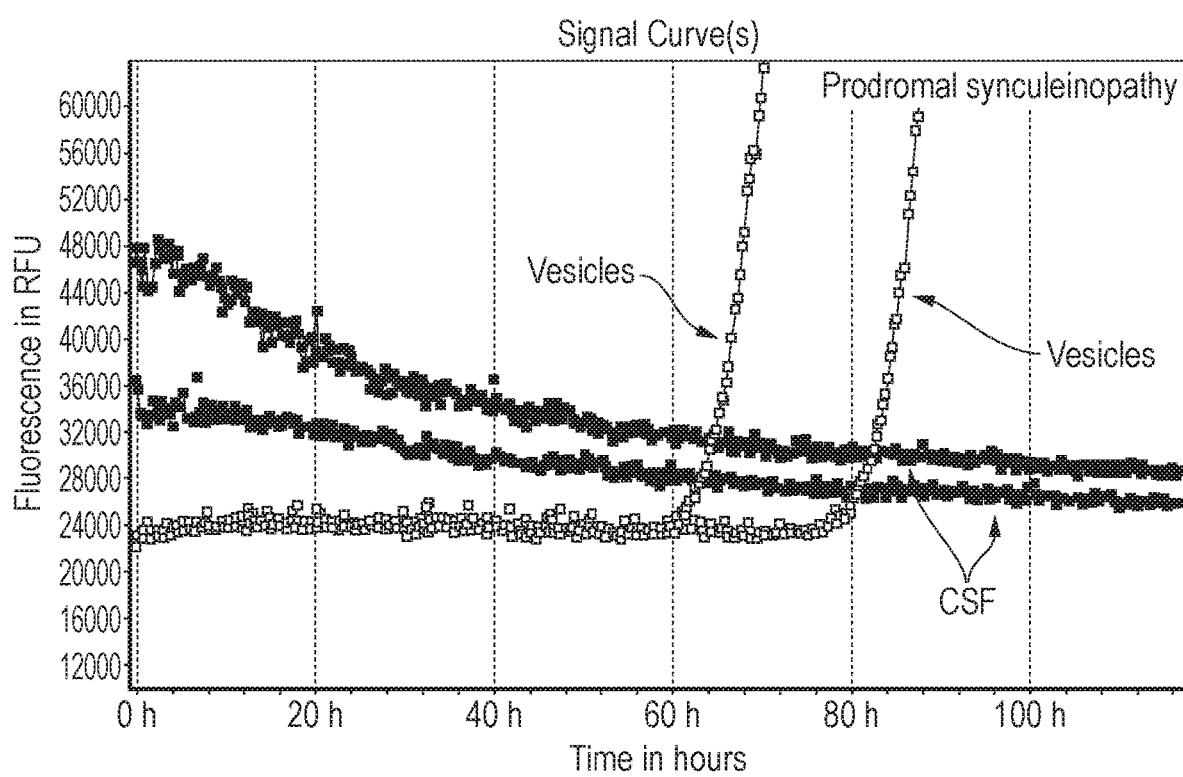

The inventors have purified EVs from brain tissue using a largely modified protocol by Perez-Gonzalez (2012). Quality check analysis was performed as per CSF EVs described earlier i.e. using TRPS and transmission electron microscopy to verify vesicles purity, concentration and size (FIG. 8). Vesicles markers were determined by Western blotting (FIGS. 9 and 10). The absence of calnexin proves the vesicle purity and lack of contamination with cellular material. The inventors detected forms of some neuronal vesicular proteins i.e. synaptophysin and snap25, and very small amount of mitochondrial protein TFAM that seem to be associated with vesicles (note the absence of porin that is a mitochondrial membrane marker which proves absence of whole mitochondria within vesicles), immuno-electron microscopy may be used to determine their location in relation to EVs (in vesicles or bound). The inventors detected alpha-synuclein in vesicle fractions in patients and controls and quantified it using ELISA (FIG. 11). No significant changes in levels of alpha-synuclein were detected.

RTQUIC

An RTQUIC assay was performed using purified CSF vesicles and unprocessed CSF. The assay showed 100% sensitivity and 100% specificity when using purified vesicles. Moreover a prodromal case of disease was detected (clinically a control without any parkinsonism or memory impairment, however mild neuropathological changes could be seen in the brain that are suggested to progress over time to a clinically manifest disease). Protocol for RTQUIC as published before in Fairfoul 2016. Positive control for the assay shown in FIG. 13.

Ongoing Work on Blood Vesicles

Figure 13:
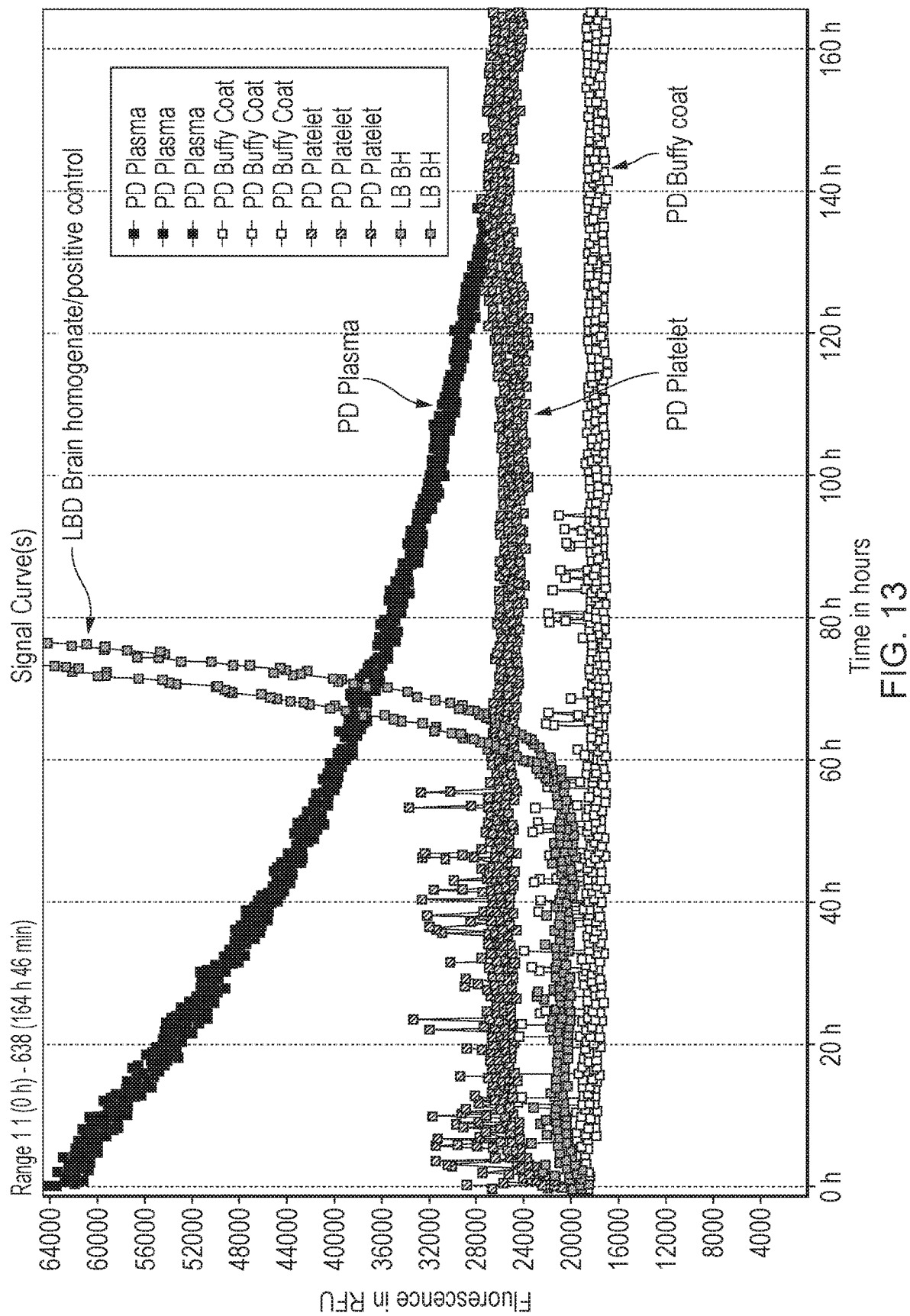
FIG. 13 shows the results of unprocessed Parkinson's disease plasma, platelets and buffy coat RT-QUIC.
Figure 14:
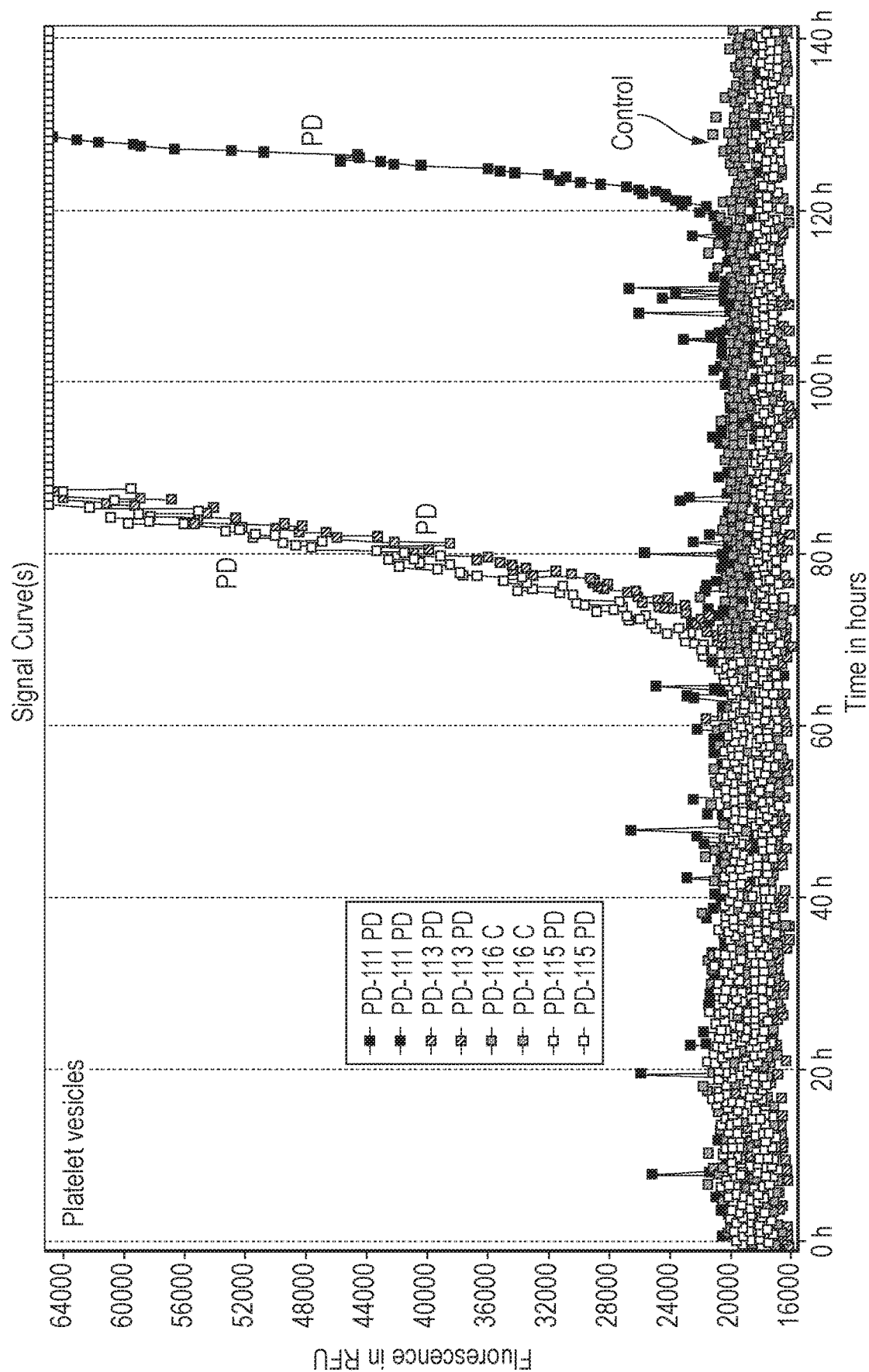
FIG. 14 shows the results of RT-QUIC with purified platelet vesicles.
Figure 15:
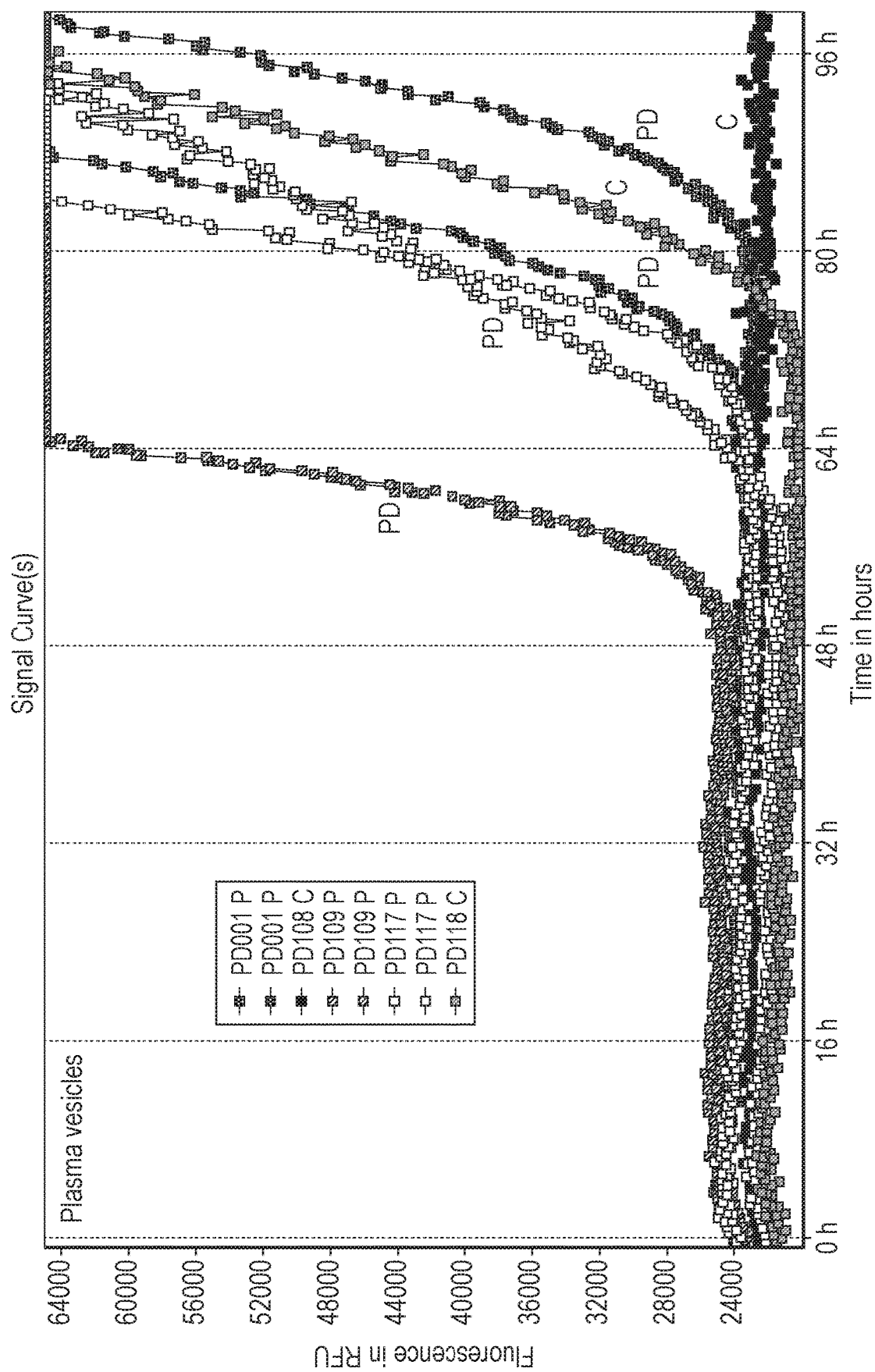
FIG. 15 shows the results of RT-QUIC with purified plasma vesicles.

Previous studies using RTQUIC did not detect alpha-synuclein pathology when unprocessed plasma, platelets or buffy coat were used (FIG. 13). The inventors have now used RTQUIC on their purified EV samples derived from plasma and platelets and their representative data are shown in FIGS. 14 and 15. Using plasma derived extracellular vesicles significantly improves the disease signal detection. Advantageously, using the method described herein the inventors are able to detect a positive signal from a sample which might be a preclinical case of disease.

Further Examples (Referring to FIGS. 16 to 22)

6 samples of post-mortem CSF were tested from individuals with clinical and neuropathological diagnosis of: Parkinson's disease (PD, 1 sample), dementia with Lewy bodies (DLB, 3 samples) and healthy controls (2 samples). Parkinson's disease brain homogenate and DLB and control extracellular vesicles isolated from the frontal cortex were also tested.

7 urine samples from individuals with a clinical diagnosis of either multiple system atrophy (MSA), corticobasal syndrome (CBS), progressive supranuclear palsy (PSP, Steele-Richardson-Olszewski syndrome), or healthy control were also tested.

Figure 16:
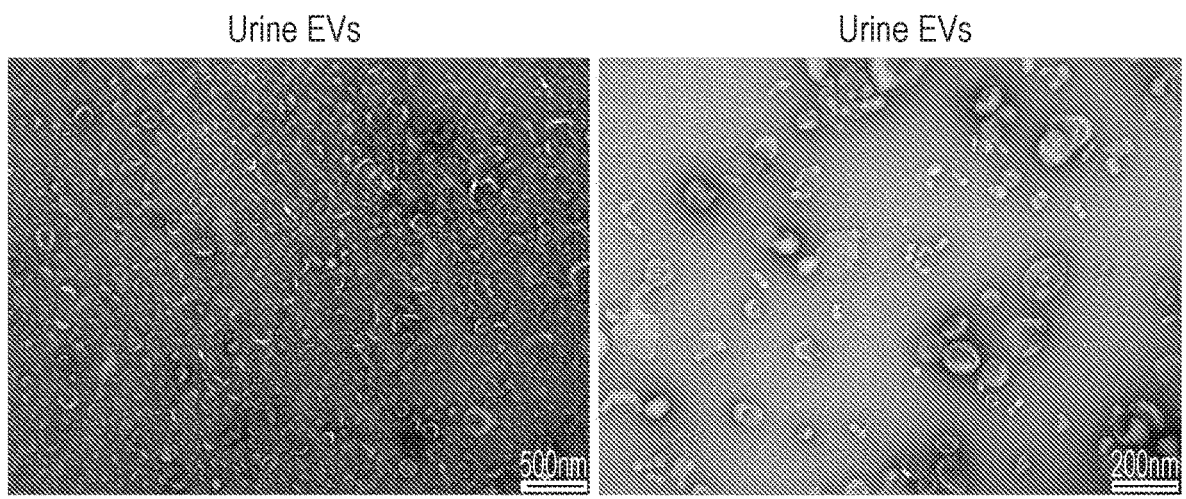
FIG. 16 shows TEM images of extracellular vesicles purified from human urine.
Figure 17:
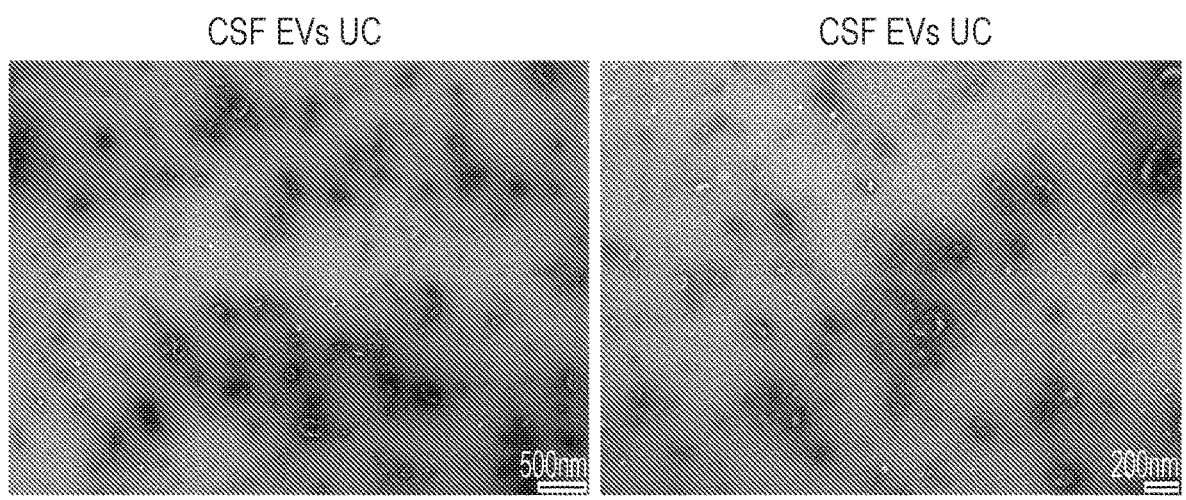
FIG. 17 shows TEM images of extracellular vesicles purified from human post-mortem CSF using ultracentrifugation.
Figure 18:
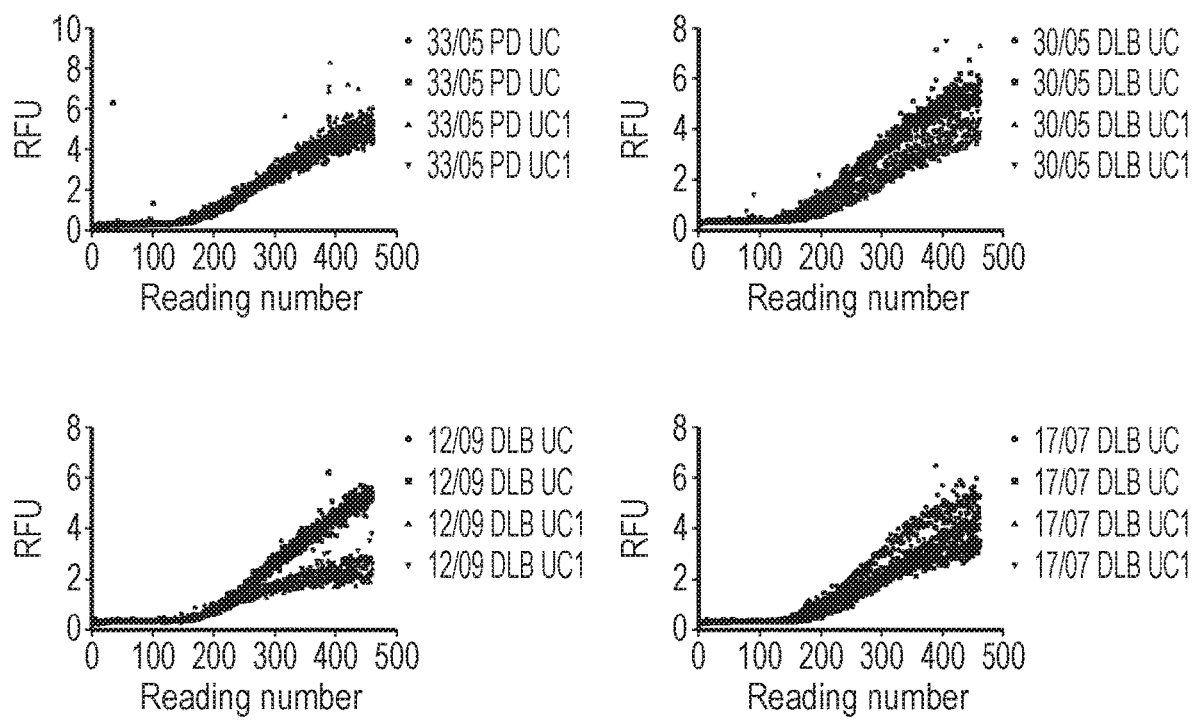
FIG. 18 shows results of protein aggregation assay using extracellular vesicles isolated by means of ultracentrifugation for dementia with Lewy bodies and Parkinson's disease CSF samples. Measurements were taken every 15 minutes over the course of 115 hours. PD-Parkinson's disease, DLB—dementia with Lewy bodies, UC-ultracentrifugation.
Figure 19:
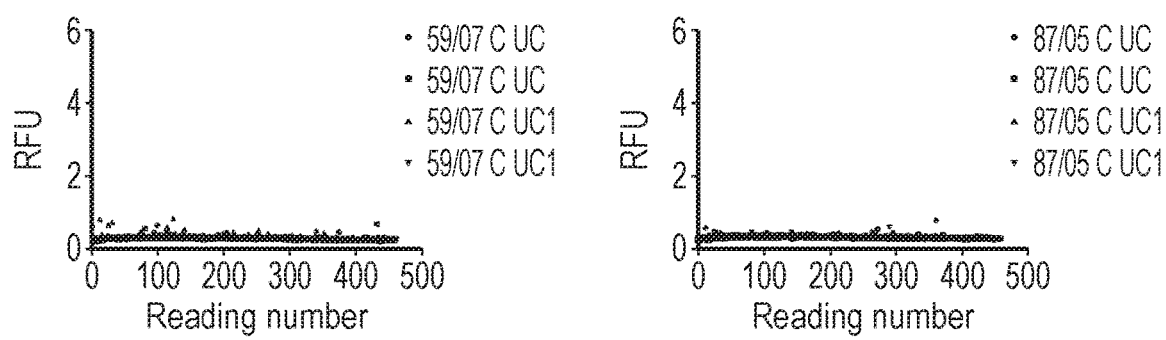
FIG. 19 shows results of protein aggregation assay using extracellular vesicles isolated by means of ultracentrifugation for healthy control samples. C— Control, UC—ultracentrifugation.
Figure 20:
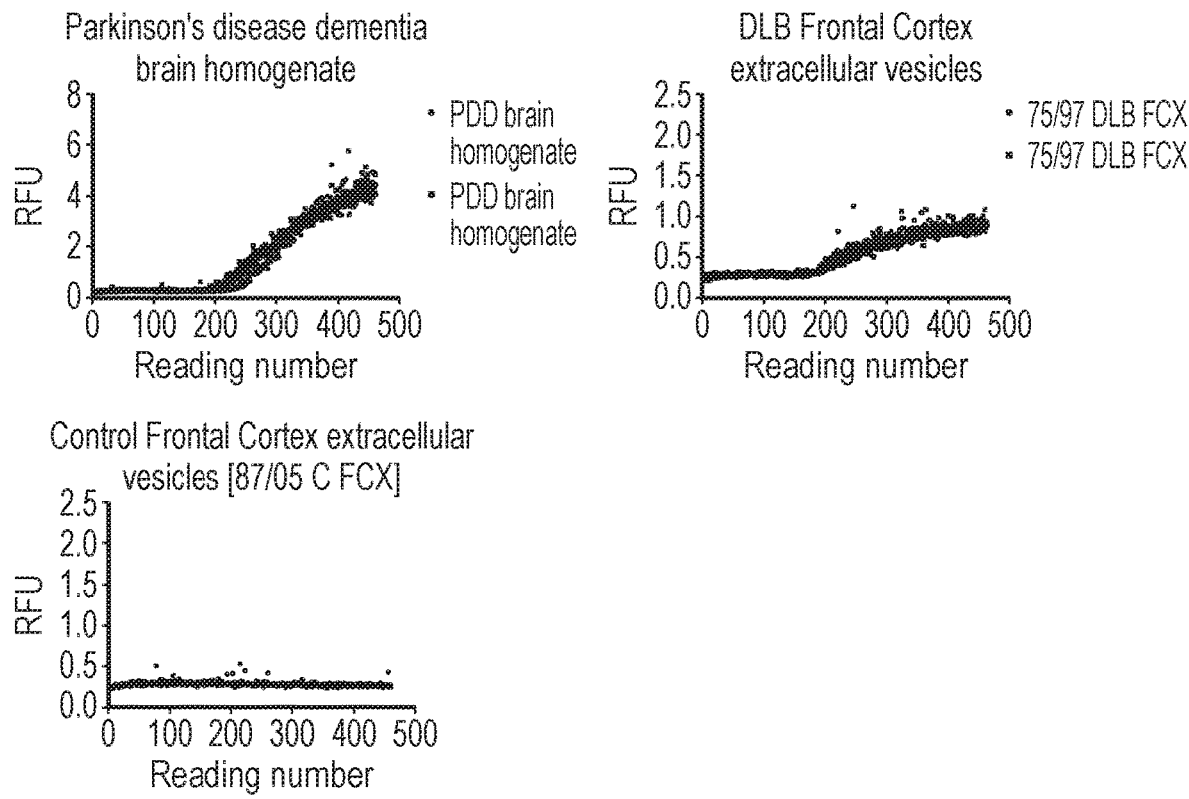
FIG. 20 shows results of protein aggregation assay using Parkinson's disease dementia brain homogenate, Dementia with Lewy bodies Frontal Cortex extracellular vesicles and control Frontal Cortex extracellular vesicles. PDD—Parkinsons's disease dementia, DLB-dementia with Lewy bodies, C— Control.

Extracellular vesicles were successfully purified from human urine samples using SEC and human post-mortem CSF samples using ultracentrifugation as verified by transmission electron microscopy (FIGS. 16 and 17).

Figure 21:
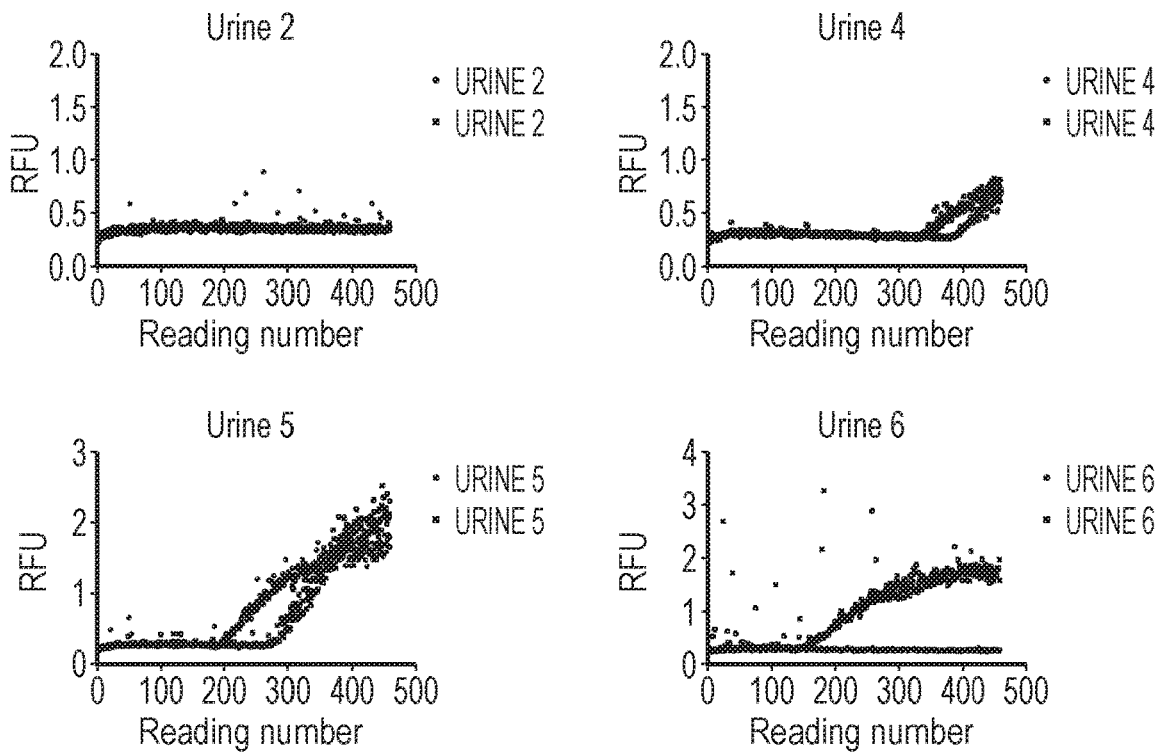
FIG. 21 shows blinded analysis of urine extracellular vesicles analysis. Donors diagnosed clinically as: Urine 2—Control; Urine 4—PSP; Urine 5—MSA; Urine 6—PSP. These data demonstrate that alpha-synucleinopathies can be positively identified from urine samples (see urine 5—MSA where both replicates provided a positive result in the alpha-synuclein protein aggregation assay, compared to control). The urine samples are taken from living patients who have clinical diagnosis but where no neuropathology has yet been carried out. Based on the results shown in FIG. 21, the inventors suspect that there is a small amount of alpha synuclein pathology present in the patient of urine 4, as both replicates are positive but the signal appears later compared to MSA urine 5. Urine 6 is potentially a false positive as one of the replicates is negative (i.e. the replicates do not show a consistent pattern).
Figure 22:
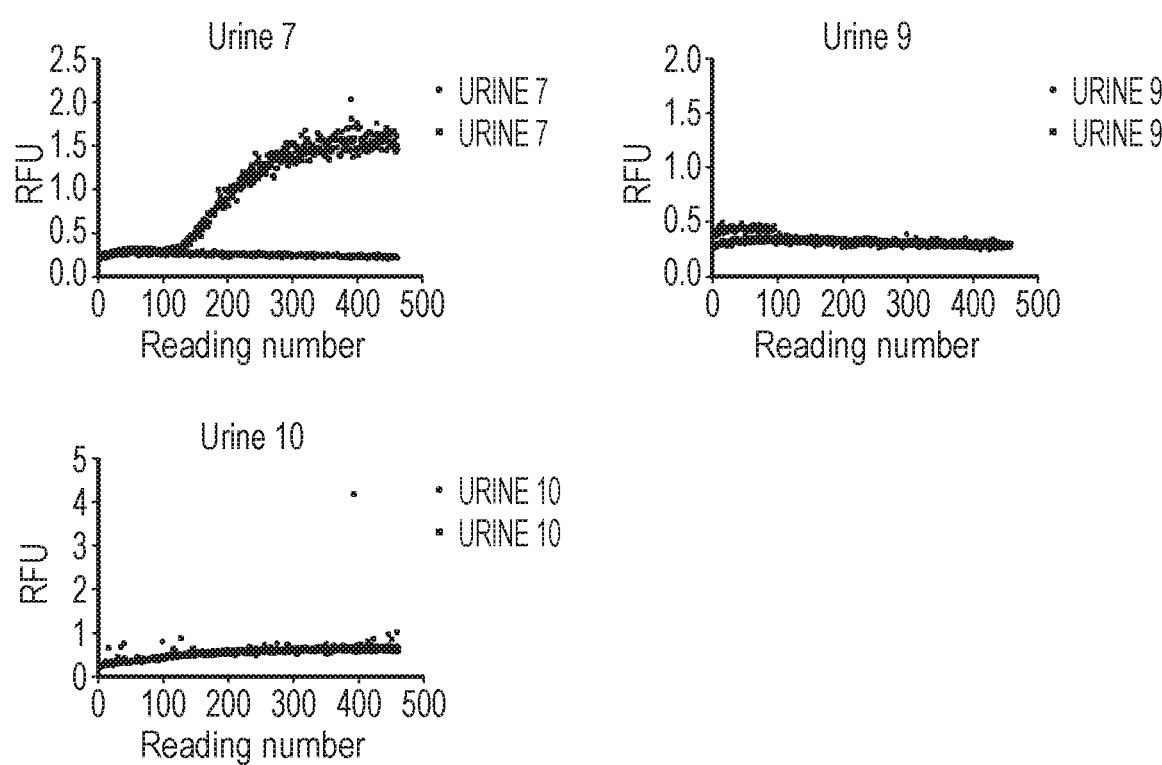
FIG. 22 shows blinded analysis of urine extracellular vesicles. Donors diagnosed clinically as: Urine 7—Control; Urine 9—PSP; Urine 10—PSP. The urine samples are taken from living patients who have clinical diagnosis but where no neuropathology has yet been carried out. Accordingly, some controls may in fact some pathology but not be showing clinical signs yet (see, notably, urine 7, where one of the replicates did show some positive signal in the alpha-synuclein protein aggregation assay—alternatively, this may be a false positive as one of the replicates is negative (i.e. the replicates do not show a consistent pattern)).

Protein aggregation assay results were as follows:
1. Post-mortem CSF samples—100% specificity in detecting Lewy body pathology in all 4 replicates analysed per sample (FIGS. 18, 19 and 20).
2. Urine samples—samples were analysed blinded to the disease state. (FIGS. 21 and 22). The results show that the inventors were able to positively identify the MSA case in both replicates.

Materials and Methods:

Purification of Extracellular Vesicles from Post-Mortem CSF and Plasma:

Frozen CSF, plasma and platelets were thawed on ice and vortexed vigorously to bring everything what might have attached to the walls of the tube back in the solution. CSF and plasma are pre-cleared by centrifugation; CSF 1500 g, 3000 g and 10,000 g, each step 10 mins; plasma 1500 g, 3000 g, 3000 g, 10 min each step.

If more than 500 ul of raw material available, the sample could be concentrated using the VivaSpin centrifugal concentrators (Sartorius) to 500 ul. 500 ul of the sample is then loaded onto the size exclusion chromatography (SEC) column. In this work the inventors have used qEV (Izon) standard 500 ul SEC columns. CSF/plasma were loaded onto the column and fractions eluted with PBS. As per the manufacturer's instructions, the first 6×500 ul fractions (collected as total 3 ml fraction) are the void volume and vesicles are contained within fractions 7, 8 and 9. All three fractions were collected to one tube and concentrated using VivaSpin 2 (Sartorius) to 500 ul. The concentrated vesicles were aliquoted to avoid freeze thaws and stored at −80 C.

Frozen Frontal Cortex Extracellular Vesicle Purification

Extracellular vesicles were purified from frozen tissue according to extensively modified protocol from Perez-Gonzalez et al. 2012. A minimum of 600 mg of frozen frontal cortex was thawed on ice and dissected. Tissue was dissociated in Hibernate E (Gibco, ThermoFisher) supplemented with 5 mM L-cysteine (Sigma) and papain (Sigma, final concentration 20 units/ml) at 37 C for 15 minutes with shaking. Hibernate E with protease inhibitor cocktail (Roche) was added to the total volume of 10 ml and tissue was gently homogenised by passing through 10 ml serological pipette. Dissociated tissue was filtered using a 40 µm mesh filter and filtrate centrifuged at 300 g-10 min, 2000 g-10 min and 10,000 g-30 min. With each step the supernatant was collected. The final supernatant was further filtered using 0.45 µm filter and concentrated to 500 µl using VivaSpin Turbo 4 centrifugal concentrators (Sartorius). This sample was applied to the SEC qEV column and processed for EVs isolation as per CSF EVs.

TRPS has been provided by Izon Science.

Electron Microscopy 5 ul of vesicle suspension in PBS has been applied to glow discharged carbon-coated copper grids for a few seconds. The grids were dried by touching a filter paper and stained with 2% uranyl acetate for a few seconds. Grids were dried. The grids were examined using a Philips CM 100 Compustage (FEI) Transmission Electron Microscope and digital images were collected using an AMT CCD camera (Deben).

Western Blot 18 ul of exosomal extracts were subjected to Western blot analysis using the Invitrogen NuPAGE 4-12% Bis-Tris gel electrophoresis system and as per the manufacturer's instructions. CD63 and CD81 were tested under non-reducing conditions. All antibodies were purchased from Abcam apart from Alix (Cell Signalling) and SNAP25 (Sigma). Antibodies were incubated with the membranes over night at 4 C, followed by appropriate secondary antibodies for 1 hour (Dako) at room temperature and developed using Pierce ECL Plus Western blotting substrate or SuperSignal West Femto Maximum Sensitivity Substrate. Signal was detected with Amersham Imager 600.

Lipidomics

EV lipids were extracted in chloroform/methanol (2/1, v/v). Global (non-targeted) lipidomic analysis was performed by liquid chromatography-mass spectrometry (LC-MS) using a high resolution Thermo Orbitrap Exactive system in positive and negative ion modes using C18 and HILIC columns. Data sets were processed (aligned, deconvoluted and normalised) using Non-Linear Dynamics Progenesis QI software. Disturbances (relative changes) in lipid profiles were determined by subjecting data sets to multivariate data analysis (principal component analysis PCA and orthogonal partial least squares-discriminant analysis—OPLS-DA) using SIMCA-P software. Lipid identifications were made by searching against LIPID MAPS (www.lipidmaps.org/), HMDB (http://www.hmdb.ca/) databases. Lipid classes were quantified by comparison to internal standards that are representative of the major lipid classes. Statistical analysis involved Shapiro-Wilk normality test followed by one-way Anova, unpaired t-test or non-parametric test according to the data set.

ImmunoEM

Performed in the EM facility, St Andrews University.

Vesicles were bound to a support and labelled with anti-alpha-synuclein antibodies (BD Transduction Laboratories) followed by electron dense gold particle marker to reveal their location. Vesicles were contrasted with heavy metals in the thin film of methylcellulose before imaging in the electron microscope.

Alpha-Synuclein ELISA

ELISA plate was coated with anti-alpha synuclein 10D2 antibodies (Analitik Jena, 1:2000) antibodies in a coating buffer (carbonate-bicarbonate buffer: 50 ml of 0.2M sodium bicarbonate+5 ml of 0.2M sodium carbonate) in a total volume of 100 µl per well overnight at 4° C. Wells were washed 3 times with phosphate buffered saline+0.2% Tween (PBST). Plate was blocked with 1% BSA in PBST, 200 µl per well, and agitated on a rocking plate for 1 h, following which it was washed once with PBST. Recombinant alpha-synuclein standards (Sigma-Aldrich; 40—0.001 ng/µl) and samples were prepared in PBS+0.2% Tween, loaded 100 µl per well and agitated on a rocking plate for 2 h. Wells were washed three times with PBST. Detection antibody αβ synuclein (Abcam, 1:1500) in 1% BSA in PBST was added (100 µl per well) and agitated on rocking plate for 1 h, followed by three washes with PBST. Conjugate Goat anti-rabbit AP (Santa Cruz, 1:1000) in 1% BSA in PBST was added in 100 µl total volume per well and agitated on rocking plate for 1 h, followed by three washes in PBST. pNPP (p-nitrophenyl phosphate; Sigma-Aldrich) substrate was added at 1 mg/ml in substrate buffer (0.05 M sodium carbonate+0.001M MgCl2 (in dH2O), and loaded 100 µl per well. Plate was incubated at 37° C. for 30 minutes and absorbance recorded at 412 nm.

RTQUIC

RTQUIC was performed as published previously in Fairfoul at al. 2016.

Further Materials and Methods (Referring to FIGS. 16 to 22):

Purification of extracellular vesicles from post-mortem cerebrospinal fluid samples using ultracentrifugation.

Frozen post-mortem cerebrospinal fluid (CSF) samples (1 ml to 1.5 ml) were defrosted on ice, vortexed vigorously and pre-cleared by centrifugation at 500×g for 10 minutes, 2000×g for 15 minutes and 17000×g for 30 minutes at 4° C., with the supernatant being subjected to centrifugation each time. Final supernatant was ultracentrifuged at 130,000×g for 1 hour at 4° C. in Optima Max-XP Ultracentrifuge Beckman Coulter using the TLA 55 S/N 17U1340 rotor. Supernatant was discarded and pellet washed with Phosphate Buffered Saline (PBS) and ultracentrifuged again at 130,000×g for 1 hour at 4° C. Supernatant was discarded and pellet resuspended in PBS with protease inhibitor cocktail (Roche). Samples were imaged using negative staining and transmission electron microscopy with Hitachi HT7800 120 kV electron microscope.

Purification of Extracellular Vesicles from Human Urine Samples.

Frozen urine samples (35 ml to 100 ml) were defrosted, vortexed vigorously and pre-cleared by centrifugation at 1500×g for 10 minutes, 3000×g for 10 minutes and 4600×g for 30 minutes at 4° C., with the supernatant being subjected to centrifugation each time. Final supernatant was concentrated using Amicon ultrafiltration units with molecular weight cut off 100 kDa (Merck Millipore) to 500 µl. Filtrate was centrifuged at 16100×g at 4° C. for 10 minutes and supernatant subjected to size exclusion chromatography (SEC) using the qEV original 70 nm SEC column (Izon) according to the manufacturer's recommendations. 1500 µl of vesicles fraction was collected and concentrated using Amicon ultrafiltration units with molecular weight cut off 3 kDa (Merck Millipore). Samples were imaged using negative staining and transmission electron microscopy with Hitachi HT7800 120 kV electron microscope.

Alpha-Synuclein Protein Aggregation Assay.

Protein aggregation assay has been performed as described previously in Fairfoul et al. (2016). Reactions were run using ThermoFisher VarioskanLUX Multimode plate reader and measurements of fluorescent signal were taken every 15 minutes over 115 hours. Post-mortem CSF samples were analysed twice in duplicates with 2 different amounts of vesicles being tested. Data was analysed using the Skanit software (ThermoFisher).

Unless defined otherwise herein, all technical and scientific terms used herein have the same meaning as commonly understood by one of ordinary skill in the art to which this invention pertains. For example, Singleton and Sainsbury, Dictionary of Microbiology and Molecular Biology, 2d Ed., John Wiley and Sons, NY (1 94); and Hale and Marham, The Harper Collins Dictionary of Biology, Harper Perennial, NY (1991) provide those of skill in the art with a general dictionary of many of the terms used in the invention. Although any methods and materials similar or equivalent to those described herein find use in the practice of the present invention, the preferred methods and materials are described herein. Accordingly, the terms defined immediately below are more fully described by reference to the Specification as a whole. Also, as used herein, the singular terms "a", "an," and "the" include the plural reference unless the context clearly indicates otherwise. Unless otherwise indicated, nucleic acids are written left to right in 5' to 3' orientation;

amino acid sequences are written left to right in amino to carboxy orientation, respectively. It is to be understood that this invention is not limited to the particular methodology, protocols, and reagents described, as these may vary, depending upon the context they are used by those of skill in the art.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent, or similar purpose, unless expressly stated otherwise. Thus, unless expressly stated otherwise, each feature disclosed is one example only of a generic series of equivalent or similar features.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

REFERENCES

McKeith et al., Neurology. 2017 Jul. 4; 89(1):88-100. Diagnosis and management of dementia with Lewy bodies: Fourth consensus report of the DLB Consortium.

Postuma et al., Mov Disord. 2015 October; 30(12):1591-601. MDS clinical diagnostic criteria for Parkinson's disease.

Han-Joon Kim et al., Journal of Neurology, August 2015, Volume 262, Issue 8, pp 1801-1813; Diagnosis and differential diagnosis of MSA: boundary issues.

Gallea et al., J Biol Chem. 2014 Sep. 26; 289(39): 26733-42. Structural insights into amyloid oligomers of the Parkinson disease-related protein α-synuclein.

Tuttle et al., Nat Struct Mol Biol. 2016 May; 23(5):409-15. Solid-state NMR structure of a pathogenic fibril of full-length human α-synuclein.

Zerr et al., APMIS. 2002 January; 110(1):88-98. Clinical diagnosis and differential diagnosis of CJD and vCJD. With special emphasis on laboratory tests.

Gallagher-Jones et al., Nat Struct Mol Biol. 2018 February; 25(2):131-134. Sub-angstrom cryo-EM structure of a prion protofibril reveals a polar clasp.

Desai et al., Neurology. 2005 Jun. 28; 64(12 Suppl 3):S34-9. Diagnosis and treatment of Alzheimer's disease.

Schmidt M et al., Proc Natl Acad Sci USA. 2015 Sep. 22; 112(38):11858-63. Peptide dimer structure in an Aβ(1-42) fibril visualized with cryo-EM.

Fitzpatrick et al., Nature. 2017 Jul. 13; 547(7662):185-190. Cryo-EM structures of tau filaments from Alzheimer's disease.

Höglinger G U et al., Mov Disord. 2017 June; 32(6):853-864. Clinical diagnosis of progressive supranuclear palsy: The movement disorder society criteria.

Salvadores et al., cell reports 7, 261-268, 2014. Detection of misfolded AB oligomers for sensitive biochemical diagnosis of Alzheimer's disease.

Loov et al., cell Mol Neurobiol 2016. Alpha-synuclein in extracellular vesicles; functional implications and diagnostic opportunities.

Fairfoul et al., Annals of Clinical and translational neurology; 2016 (pp 812-818). Alpha-synuclein RT-QUIC in the CSF of patients with alpha-synucleinopathies.

Herva et al., the journal of biological chemistry vol 289 No 17 pp 11897-11905, 2014. Anti-amyloid compounds inhibit alpha-synuclein aggregation induced by protein misfolding cyclic amplification (PMCA).

Boing et al., journal of extracellular vesicles, 3:23430; 2014. Single-step isolation of extracellular vesicles by size-exclusion chromatography.

Mollenhauer et al., lancet Neurol 2011; 10: 230-40. Alpha-synuclein and tau concentrations in cerebrospinal fluid of patients presenting with parkinsonism: a cohort study.

Danzer et al., Molecular Neurodegeneration 2012, 7:42 Exosomal cell-to-cell transmission of alpha synuclein oligomers.

Luk et al., JAMA Neurol 2016: 73 (12): 1454-1460. Diagnosing sporadic Creutzfeldt-Jakob disease by the detection of abnormal prion protein in patient urine.

Lobb et al., journal of extracellular vesicles 2015, vol 4: 27031. Optimised exosome isolation protocol for cell culture supernatant and human plasma.

Andaloussi et al., Nature Reviews Drug Discovery, vol 12, May 2013, page 347-357. Extracellular vesicles; biology and emerging therapeutic opportunities.

Atarashi et al., nature medicine vol 17 number 2, 2011. Ultrasensitive human prion detection in cerebrospinal fluid by real-time quaking-induced conversion.

Gonzalez-Montalban et al., Plos Pathogens vol 7, issue 2, 2011. Highly efficient protein misfolding cyclic amplification.

Perez-Gonzalez et al. The journal of biological chemistry vol. 287 No 51 pp 43108-43115, 2012. The exosome secretory pathway transports amyloid precursor protein carboxyl-terminal fragments from the cell into the brain extracellular space.

Stuendl et al., Brain A journal of Neurology 2016; 139; 481-494 Induction of alpha-synuclein aggregate formation by CSF exosomes from, patients with Parkinson's disease and dementia with Lewy bodies.

McKhann et al. The diagnosis of dementia due to Alzheimer's disease: recommendations from the National Institute on Aging-Alzheimer's Association workgroups on diagnostic guidelines for Alzheimer's disease. *Alzheimers Dement.* 2011; 7: 263-269

Dubois et al. Advancing research diagnostic criteria for Alzheimer's disease: the IWG-2 criteria. *Lancet Neurol.* 2014; 13: 614-629.

Isas et al., Biochemistry. 2017 Jul. 18; 56(28):3579-3586.

Pagan F, et al., Handb Clin Neurol. 2017; 144:63-67.

Traynor et al., Clinical features of amyotrophic lateral sclerosis according to the El Escorial and Airlie House diagnostic criteria: A population-based study. Arch Neurol 2000; 57:1171-1176.

Wardle et al., Mov Disord. 2009 Aug. 15; 24(11):1636-40.

van de Warrenburg et al., EFNS/ENS Consensus on the diagnosis and management of chronic ataxias in adulthood. Eur J Neurol. 2014 April; 21(4):552-62.

Sangwan S et al., Proc Natl Acad Sci USA. 2017 Aug. 15; 114(33):8770-8775. Atomic structure of a toxic, oligomeric segment of SOD1 linked to amyotrophic lateral sclerosis (ALS).

Alexander et al., Validation of the new consensus criteria for the diagnosis of corticobasal degeneration J neurol Neurosurg Psychiatry 2014: 85: 923-927

Gil D. Rabinovici and Bruce L. Miller CNS Drugs. 2010 May 1; 24(5): 375-398. Frontotemporal Lobar Degeneration: Epidemiology, Pathophysiology, Diagnosis and Management Guo Q et al., Cell. 2018 Feb. 8; 172(4):696-705. In Situ Structure of Neuronal C9orf72 Poly-GA Aggregates Reveals Proteasome Recruitment.

Basso, et al., Mutant Copper-Zinc Superoxide Dismutase (SOD1) Induces Protein Secretion Pathway Alterations and Exosome Release in Astrocytes IMPLICATIONS FOR DISEASE SPREADING AND MOTOR NEURON PATHOLOGY IN AMYOTROPHIC LATERAL SCLEROSIS JBC; 2013 Vol 288 No 22 pp 15699-15711

Hinz et al J Biol Chem. 2012 Jan. 13; 287(3):2068-78. Polyglutamine expansion alters the dynamics and molecular architecture of aggregates in dentatorubropallidoluysian atrophy.

Ruggeri et al., Nat Commun. 2015 Jul. 28; 6:7831. Infrared nanospectroscopy characterization of oligomeric and fibrillar aggregates during amyloid formation.

The invention claimed is:

1. An in vitro method of determining the presence of pathological alpha-synuclein protein in a subject, the method comprising:
   (a) providing an enriched extracellular vesicle sample from the subject; and
   (b) determining the presence of the pathological alpha-synuclein protein in the extracellular vesicle sample with a protein amplification based assay.

2. The method of claim 1, wherein the extracellular vesicle sample is from a subject that is suspected of having an alpha synucleinopathy or having an increased risk of developing the alpha synucleinopathy.

3. The method of claim 2, wherein the alpha synucleinopathy is selected from the group consisting of Parkinson's disease, Dementia with Lewy Bodies, and Multiple System Atrophy.

4. The method of claim 1, wherein the extracellular vesicle sample is obtained from a biological sample selected from CSF, blood, brain tissue homogenate, urine, saliva, or a combination thereof.

5. The method of claim 4, wherein the blood sample is selected from the group consisting of plasma, serum, platelets, and buffy coats.

6. The method of claim 4, wherein the extracellular vesicle sample is obtained using size exclusion chromatography, differential centrifugation, or density-gradient ultracentrifugation.

7. The method of claim 6, wherein the method further comprises the steps of:
   i) providing a biological sample from the subject; and
   ii) obtaining the extracellular vesicle sample from the biological sample using size exclusion chromatography.

8. The method of claim 1, wherein the a protein amplification based assay is real-time quaking-induced conversion (RT-QuIC), or protein misfolding cyclic amplification (PMCA).

9. The method of claim 4, wherein the extracellular vesicle sample is obtained from a cerebral spinal fluid sample using size exclusion chromatography.

* * * * *